(12) United States Patent
Peyser et al.

(10) Patent No.: US 10,610,807 B2
(45) Date of Patent: Apr. 7, 2020

(54) STERILIZING CHROMATOGRAPHY COLUMNS

(71) Applicant: Repligen Corporation, Waltham, MA (US)

(72) Inventors: James Ronald Peyser, Billerica, MA (US); Dana Cristina Pentia, Arlington, MA (US)

(73) Assignee: Repligen Corporation, Waltham, MA (US)

( * ) Notice: Subject to any disclaimer, the term of this patent is extended or adjusted under 35 U.S.C. 154(b) by 584 days.

(21) Appl. No.: 15/109,735

(22) PCT Filed: Jan. 16, 2015

(86) PCT No.: PCT/US2015/011839
§ 371 (c)(1),
(2) Date: Jul. 5, 2016

(87) PCT Pub. No.: WO2015/109246
PCT Pub. Date: Jul. 23, 2015

(65) Prior Publication Data
US 2016/0325204 A1 Nov. 10, 2016

Related U.S. Application Data

(60) Provisional application No. 61/929,008, filed on Jan. 17, 2014.

(51) Int. Cl.
*B01D 15/20* (2006.01)
*A61L 2/08* (2006.01)
(Continued)

(52) U.S. Cl.
CPC ............ *B01D 15/206* (2013.01); *A61L 2/081* (2013.01); *A61L 2/087* (2013.01); *B01D 15/20* (2013.01);
(Continued)

(58) Field of Classification Search
CPC ...... A61L 2/081; A61L 2/087; A61L 2022/11; B01D 15/00; B01D 15/08; B01D 15/10;
(Continued)

(56) References Cited

U.S. PATENT DOCUMENTS

| 5,151,350 A | 9/1992 | Colbert et al. |
| 6,620,326 B1 | 9/2003 | Lihme et al. |

(Continued)

FOREIGN PATENT DOCUMENTS

| CN | 104117226 | 10/2014 |
| GB | 2476580 | 6/2011 |

(Continued)

OTHER PUBLICATIONS

International Search Report and Written Opinion in International Application No. PCT/US2015/011839, dated Apr. 30, 2015, 12 pages.

(Continued)

*Primary Examiner* — Kara M Peo

(57) ABSTRACT

If one sterilizes pre-packed, plastic chromatography columns with an appropriate level of gamma irradiation, the resulting sterile chromatography columns maintain sufficient packing media function and maintain column mechanical properties and pressure ratings.

1 Claim, 19 Drawing Sheets

(51) Int. Cl.
*B01D 15/32* (2006.01)
*B01D 15/36* (2006.01)
*B01D 15/38* (2006.01)

(52) U.S. Cl.
CPC ......... *A61L 2202/11* (2013.01); *B01D 15/327* (2013.01); *B01D 15/361* (2013.01); *B01D 15/3809* (2013.01)

(58) Field of Classification Search
CPC .... B01D 15/20; B01D 15/203; B01D 15/206; B01D 15/22; B01D 15/327; B01D 15/361; B01D 15/3809
See application file for complete search history.

(56) References Cited

U.S. PATENT DOCUMENTS

| | | |
|---|---|---|
| 2010/0219115 A1 | 9/2010 | Davis et al. |
| 2011/0006878 A1 | 1/2011 | Nyffeler et al. |
| 2011/0118442 A1 | 5/2011 | Engstrand et al. |
| 2011/0275559 A1 | 11/2011 | Ostergaard et al. |
| 2013/0001147 A1 | 1/2013 | Salomonsson et al. |
| 2013/0062267 A1 | 3/2013 | Gebauer |
| 2013/0193052 A1 | 8/2013 | Witt et al. |

FOREIGN PATENT DOCUMENTS

| | | |
|---|---|---|
| JP | H03-168150 | 7/1991 |
| JP | 2004-180569 | 7/2004 |
| JP | 2005-503239 | 2/2005 |
| JP | 2005-363652 | 11/2005 |
| JP | 2006-300965 | 11/2006 |
| JP | 2008-518885 | 6/2008 |
| JP | 2009-053191 | 3/2009 |
| JP | 2010-504754 | 2/2010 |
| JP | 2010-518376 | 5/2010 |
| JP | 2010-156687 | 7/2010 |
| JP | 2011-518369 | 6/2011 |
| JP | 2013-515251 | 5/2013 |
| JP | 2013-515258 | 5/2013 |
| JP | 2013-527473 | 6/2013 |
| JP | 2013-237452 | 11/2013 |
| WO | WO 03026703 | 4/2003 |
| WO | WO 2006/043895 | 4/2006 |
| WO | WO 2008/039141 | 4/2008 |
| WO | WO 2008/094237 | 8/2008 |
| WO | WO 2009/120231 | 10/2009 |
| WO | WO 2011/078772 | 6/2011 |
| WO | WO 2011/152788 | 12/2011 |
| WO | WO2013/116367 | 8/2013 |
| WO | WO 2013/180633 | 12/2013 |
| WO | WO2015/109246 | 7/2015 |

OTHER PUBLICATIONS

International Preliminary Report on Patentability in International Application No. PCT/US2015/011839, dated Jul. 19, 2016, 9 pages.
Chinese Office Action in Chinese Application No. 201580004874.7, dated Mar. 13, 2017, 7 pages.
'www.gelifesciences.co' [online]. "GE Healthcare: Capto MMC," Aug. 1, 2012, [retrieved on Jul. 21, 2017]. Retrieved from the Internet: URL http://www.gelifesciences.co.jp/newsletter/downstream/pdf/11003545aa.pdf. 6 pages.
Japanese Office Action in Japanese Application No. 2016-547015, dated Aug. 22, 2017, 16 pages, with English translation.
'ip.com' [online]. "Method for radiation sterilization of sensitive chromatographic resins and membranes", Sep. 2009, Retrieved from the Internet URL https://priorart.ip.com/IPCOM/000188023. 2 pages.
Chinese Office Action in Chinese Application No. 201580004874.7, dated Mar. 13, 2017, 14 pages (with English translation).
European Search Report and Written Opinion in Application No. 15737910.8, dated Aug. 18, 2017, 11 pages.

STERILIZING CHROMATOGRAPHY COLUMNS

CLAIM OF PRIORITY

This application is a 371 U.S. National Phase Application of PCT/US2015/011839, filed on Jan. 16, 2015, which claims the benefit of U.S. Patent Application Ser. No. 61/929,008, filed on Jan. 17, 2014. The entire contents of the foregoing are hereby incorporated by reference.

TECHNICAL FIELD

This disclosure relates to sterilization of chromatography columns.

BACKGROUND

Column chromatography is a separation and/or purification technique in which a stationary "bed" of a packed medium is contained within a rigid tube or column. The packing medium can be in the form of particles of a solid ("stationary phase") or a solid support material coated with a liquid stationary phase. Either way, the packing medium typically fills the inside volume of the column tube.

In separation chromatography, as a liquid sample ("mobile phase") passes through the column, different compounds in the sample can associate differentially with the stationary phase such that they are slowed relative to the mobile phase and move through the column at different speeds. Thus, those compounds that associate more with the stationary phase move more slowly through the column than those that associate less, and this speed differential results in the compounds being separated from one another as they pass through and exit the column.

In affinity chromatography, the packing medium includes binding agents, such as antigens, antibodies, or ligands, that specifically bind to one or more desired compounds or molecules in the liquid sample. Thus, as the liquid sample flows through the packing medium only the desired compounds or molecules remain in the column. A subsequent flow through the packing medium of an eluting liquid separates the desired compounds or molecules from the binding agents attached to the packing medium, or separates the binding agents from the packing medium. Either way, the desired compounds or molecules are rinsed out of the column and collected in the eluting fluid. Affinity chromatography can be used in a number of applications, including nucleic acid purification, protein purification from cell free extracts, and purification from blood.

New developments in bioprocessing, such as continuous processing and multi-product processing, require increased stringency in microbial control. Sterile flow paths from cell culture into downstream purification are needed to reduce the risk of contamination. Thus, it would be of great utility to be able to make sterile, disposable columns that maintain high levels of performance.

SUMMARY

The invention is based, at least in part, on the discovery that if one irradiates plastic chromatography columns with a certain range of gamma irradiation, e.g., 8.0 to 35 or 40 kGy, they will be sterilized to differing Sterility Assurance Levels (SALs), while still maintaining significantly useful function. For example, even under high levels of irradiation of up to 35 or 40 kGy, plastic columns maintain their initial pre-gamma irradiation pressure ratings and mechanical properties following irradiation. In addition, columns containing a packing medium that includes a covalently coupled affinity ligand, e.g., immobilized Protein A, maintain suitable performance after being treated with the sterilization methods described herein. The methods described herein inhibit or avoid any reduction in the affinity capture performance of binding agents, e.g. Protein A, used to modify packing media, which may be typically caused by irradiation, by including specific additives to a protective solution that is filled into the column to protect the packing medium during irradiation.

In one aspect, the disclosure features methods of making and packing chromatography columns and then sterilizing those columns using the specific techniques and parameters recited herein. These methods include (a) selecting a column tube, e.g., of plastic material or another appropriately elastic material, that has an appropriate inner diameter and length to accommodate a desired volume of packing medium; (b) adding a packing medium, e.g., agarose or silica beads or any other appropriate chromatography packing medium, e.g., covalently coupled to a functionalizing or binding agent, such as Protein A, for example, the full-length wild-type *Staphylocuccus* protein A (SpA) or a recombinant form of Protein A; (c) enclosing the packed medium as a packed bed within the tube by closing the tube with a cap or seal that can, for example, be applied as a "press fit" or "interference fit" within the tube to obtain a sealed packed bed of medium; (d) optionally, enclosing or sealing the packed column within an airtight and watertight container, e.g., a plastic bag, cylinder, or box; and (e) irradiating the column within the container with a dose of from at least 8 kGy to about 35 or 40 kGy, e.g., at least 10, 15, 20, 25, 30, 33, 35, or 40 kGy, of gamma radiation.

The column, optionally still within the airtight container, is then removed from the source of radiation, and can be transported within the sealed container, thereby maintaining the internal and external sterility of the column. The airtight and watertight container is needed only if the exterior surface of the column needs to be maintained sterile. Even without such a container, the interior of the sterilized column and the packing medium will remain sterile if the inlets and outlets of the column remain sealed.

This level of irradiation produces a sterile packed column that can be described in terms of a sterility assurance level (SAL). The SAL is the probability of a single unit, e.g., a single packed column, being non-sterile after it has been subjected to sterilization and the SAL depends on the dose of radiation and the intrinsic bioburden of the material prior to irradiation. Items with a low bioburden such as the column components described herein will attain a sterility assurance level of $10^{-6}$ organisms/unit, which is a relatively high level of sterility (only one unit, e.g., one column, out of 1 million units that have been sterilized will be non-sterile), when using a dose of 25 kGy. If there is a higher initial bioburden on the packed column before irradiation, a higher level of gamma radiation, e.g. 30 to 40 kGy can be used to achieve this same SAL. Another, somewhat lower, yet still useful, level of sterility is $10^{-3}$ organisms/unit that can be achieved when using a dose of 8 kGy (see Guide to Irradiation and Sterilization Validation of Single-Use Systems, Bioprocess International, 2008 and references within). Other levels include $10^{-4}$ organisms/unit and $10^{-5}$ organisms/unit.

In various implementations of these methods, the plastic materials can include polypropylene, polyethylene, polyamides, acetals, glass-filled plastics, carbon filled plastics, glass-fiber plastics, or carbon-fiber plastics, or carbon-fiber plastics. The packing medium can include agarose, silica, ceramic, or a polymer of acrylate or cellulose based material.

In some embodiments the packing medium can be functionalized with one or more of the following: ion exchange groups; multimodal groups possessing hydrophobic and charged properties; metal chelate groups; hydrophobic groups; or *Staphylococcus* protein A (SpA) polypeptides capable of binding to immunoglobulin IgG. For example, the ion exchange groups can include one or more of quaternary amines, sulfates, and caroboxylates and the hydrophobic groups can include one or more of propyl, octyl, and phenyl groups.

In addition, in various implementations, the SpA polypeptides can include a full-length wildtype SpA, a recombinant SpA, a monomeric SpA polypeptide comprising a SpA domain selected from SpA domains A, B, C, D, E, or Z, or a multimeric SpA polypeptide comprising any two, three, four, five, or more SpA domains, in any combination, selected from SpA domains A, B, C, D, E, or Z, or a functional equivalent thereof. For example, the SpA polypeptide can be a multimeric SpA polypeptide, e.g., the multimeric SpA polypeptide can include four or five SpA domains selected from SpA domains B, C, and Z. For example, all of the SpA domains can be the same, all three, four, or five SpA domains can be a C domain.

In various embodiments, the sterile column production methods described herein can further include selecting appropriately sized first and second flow distributors, wherein at least the second flow distributor (or both the first and the second flow distributors) has a diameter that is larger than the inner diameter of the tube, e.g., about 0.25 to 5.0% larger than the inner diameter of the tube; permanently securing the first flow distributor to a first end of the tube; after adding a packing medium into the column tube, inserting the second flow distributor into a second end of the tube by applying an axial force to drive the second flow distributor into the column tube to establish an interference fit, e.g., to thereby induce a hoop tension, that is sufficiently effective to from a sealed, e.g., a hydrostatically sealed, chamber within the tube between the first and second flow distributors; adjusting the longitudinal position of the second flow distributor within the tube by (i) applying an additional axial force to the second flow distributor until it reaches a desired location within the column tube, or (ii) forcing liquid into the chamber to apply a hydraulic force to move the second flow distributor back towards the second end of the tube, or any combination of (i) and (ii); and when the second flow distributor is properly positioned, permanently securing the second flow distributor within the tube.

In certain implementations, the packing medium can be a slurry that comprises about 40% to about 70% solids in a suitable buffer. Once the packing medium is packed into a column, a protective solution can be added. The protective solution may contain buffers or other additives that can influence the functional properties of the packed medium. For example, as described herein, aromatic alcohols added at low percent (V/V) to the protective solution can preserve affinity capture performance of gamma sterilized packed medium functionalized with a binding agent such as Protein A.

In various implementations, the protective solution added to the packing medium in the column can include from 0.1 to 25.0 percent (volume/volume) of an alcohol. For example, in some embodiments the protective solution includes from 0.1 to 5.0 percent (volume/volume) of the alcohol, wherein the alcohol comprises an aromatic alcohol such as benzyl alcohol. In other embodiments, the protective solution includes from 2.0 to 25.0 percent (volume/volume) of the alcohol, wherein the alcohol comprises an aliphatic primary alcohol such as ethanol.

In another aspect, the disclosure features the sterile chromatography columns themselves. These sterile packed chromatography columns include (a) a sterile hollow tube having two ends; and (b) a sterile packed chromatography medium within the tube, wherein the tube is closed at both ends to create a packed column; wherein the packed column has a Sterility Assurance Level (SAL) of $10^{-3}$ organisms/column. In some implementations the SAL is $10^{-6}$ organisms/column.

In these sterile packed chromatography columns, the chromatography column comprises the tube, a first flow distributor, and a second flow distributor, and these components can each be made of the same or different plastic materials. The plastic materials can include one or more of polypropylene, polyethylene, polyamides, acetals, glass-filled plastics, carbon filled plastics, glass-fiber plastics, or carbon-fiber plastics, or carbon-fiber plastics.

In various embodiments, the packing medium in the columns can include agarose, silica, ceramic, or a polymer of an acrylate or cellulose-based material. In certain implementations, the packing medium is functionalized with one or more of the following: ion exchange groups; multimodal groups possessing hydrophobic and charged properties; metal chelate groups; hydrophobic groups; or *Staphylococcus* protein A (SpA) polypeptides capable of binding to immunoglobulin IgG. For example, ion exchange groups can include one or more of quaternary amines, sulfates, and caroboxylates, and the hydrophobic groups can include one or more of propyl, octyl, and phenyl groups.

In some embodiments the SpA polypeptides can include a full-length wildtype SpA, a recombinant SpA, a monomeric SpA polypeptide comprising a SpA domain selected from SpA domains A, B, C, D, E, or Z, or a multimeric SpA polypeptide comprising any two, three, four, five, or more SpA domains, in any combination, selected from SpA domains A, B, C, D, E, or Z, or a functional equivalent thereof. For example, the SpA polypeptide can be a multimeric SpA polypeptide, e.g., including four or five SpA domains selected from SpA domains B, C, and Z. For example, the SpA domains can all be the same, e.g., the multimeric SpA polypeptide can include three, four, or five SpA domains C.

In certain embodiments, the two ends of the tube are closed by flow distributors having an outer diameter that is slightly larger than an inner diameter of the tube to provide an interference fit. In addition, in any of the embodiments and implementations described herein, the columns can be sealed within an airtight and watertight container before irradiation, as described herein. In addition, the columns can also be further sealed within a second airtight and watertight container to provide a double layer of enclosure prior to gamma irradiation. Thus, the endproduct is a sterile pre-packed, plastic chromatography column sealed within an airtight and watertight container. These highly functional and economical columns can be considered to be disposable, but have the functional integrity to be reused multiple times In some implementations, the disclosure features sterile packed chromatography columns that include a sterile hollow tube having a first end and a second end; a sterile first flow distributor secured to a first end of the tube; a sterile second flow distributor having an external diameter that is greater than an internal diameter of the tube; and a sterile packing medium filled in the tube between the first and second flow distributors; wherein the second flow distributor is secured within the second end of the tube to form a chamber within the hollow tube between the first and second flow distributors that is filled with the packing medium; and wherein the packed chromatography column has a Sterility Assurance Level of $10^{-3}$ or $10^{-6}$ organisms/column.

The packing medium in these sterile chromatography columns can have a specific adsorption level of at least 60% of a specific adsorption level of a same type of packing medium in a column that has not been irradiated with gamma irradiation. In addition, in various embodiments the packing medium can contain from 0.5 to 5.0 percent (volume/volume) of an aromatic alcohol or 2.0 to 25 percent (volume/volume) of an aliphatic primary alcohol. For example, the packing medium can contain from 0.5 to 3.0 percent (volume/volume) of benzyl alcohol or from 2.0 to 20% of ethanol.

In some embodiments, the plastic tube further has an increased end diameter $D_{Te}$ to form a chamfer at the first end, wherein the first flow distributor has an external diameter $D_{fd}$ that is greater than $D_{Ti}$, and wherein the first flow distributor is secured within the first end of the tube with an interference fit directly resulting in sufficient induced hoop tension. In certain embodiments, the first flow distributor is permanently bonded to the tube or both the first and second flow distributors can be secured to the inner wall of the tube with a permanent bond such as a welded joint.

In certain embodiments, the new chromatography columns including the packing medium within the chamber in the column or tube can be hydrostatically sealed. In certain embodiments, the chamber is constructed to withstand an internal pressure that is at least 50 pounds per square inch. In some embodiments, all three of these features are present. In some embodiments the plastic tube and the second flow distributor are made of the same type of plastic and the first flow distributor is an integral feature of the tube.

As used herein, the term "plastic" refers to a chromatography column or components of a chromatography column made from various polymeric materials, such as thermoplastics, e.g., acrylonitrile butadiene styrene (ABS), acrylic, e.g., polymethylmethacrylate (PMMA), polyolefins, polypropylene (PP), polyvinyl chloride (PVC), polytetrafluoroethylene (PTFE), polycarbonates, and various plastic composites that are made of two or more different types of plastic and/or polymeric materials, as well as thermosetting plastics, e.g., epoxy resins and fiber (e.g., glass, metal (e.g., stainless steel), or carbon fiber) reinforced plastics.

As used herein, the term "bed height" refers to the linear height of a bed of packing medium contained within a completed chromatography column.

As used herein, a "packing medium" is a slurry or suspension of a solid material in the form of irregularly-shaped or spherical particles that later form the "packed bed" in a column. The packing medium can be made from a variety of materials such as silica, ceramic, agarose, acrylic, or cellulosic polymers. The solid material can be functionalized with molecular features providing, for example, ionic, hydrophobic, or specific affinity features (e.g., with a binding agent such as antibodies or Protein A).

As used herein, a "packed bed" refers to a final state of chromatography packing medium within a chromatography column. This final state is achieved in a variety of ways. For example, one method is to combine fluid flow followed by axial compression of the bed by one or both of the flow distributors. Other methods known in the art include gravity settling of particles, vibration settling, and/or mechanical axial compression alone. Following packing, the packed bed remains hydrated in a protective solution typically containing an antimicrobial additive. As described herein, this protective solution can also or alternatively contain one or more buffers or other additives that can help protect the integrity or performance of the functionalized solid support against detrimental effects of gamma irradiation. For example, the protective solution can contain a low percent (V/V) of an aliphatic or aromatic alcohol such as ethanol or benzyl alcohol, or a polyol such as a sugar alcohol, to enhance preservation of chromatographic performance of the medium after irradiation.

As used herein, a "bed support" is a net, screen, mesh, or frit that allows the passage of various liquids yet retains the small particles of packing medium that comprises the packed bed. These bed supports can be directly connected to the flow distributors.

As used herein, the terms "permanent bond" and "permanently bonded" are used to indicate that such a bond between two components cannot be separated other than by breaking the bond or one or both of the bonded components (e.g., a tube and a flow distributor).

The new methods and systems described herein provide numerous advantages and benefits. For example, the new methods enable the preparation of pre-packed, disposable columns with fully customizable and variable bed heights and diameters, and with a desired SAL, yet have a fully functional packing medium. It was surprising that the gamma irradiation methods described herein did not significantly reduce the performance of the packing media or binding agents, and did not create or extract any contaminants or cause such contaminants to be leached from the materials used to assemble the chromatography columns after use in standard aqueous buffers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
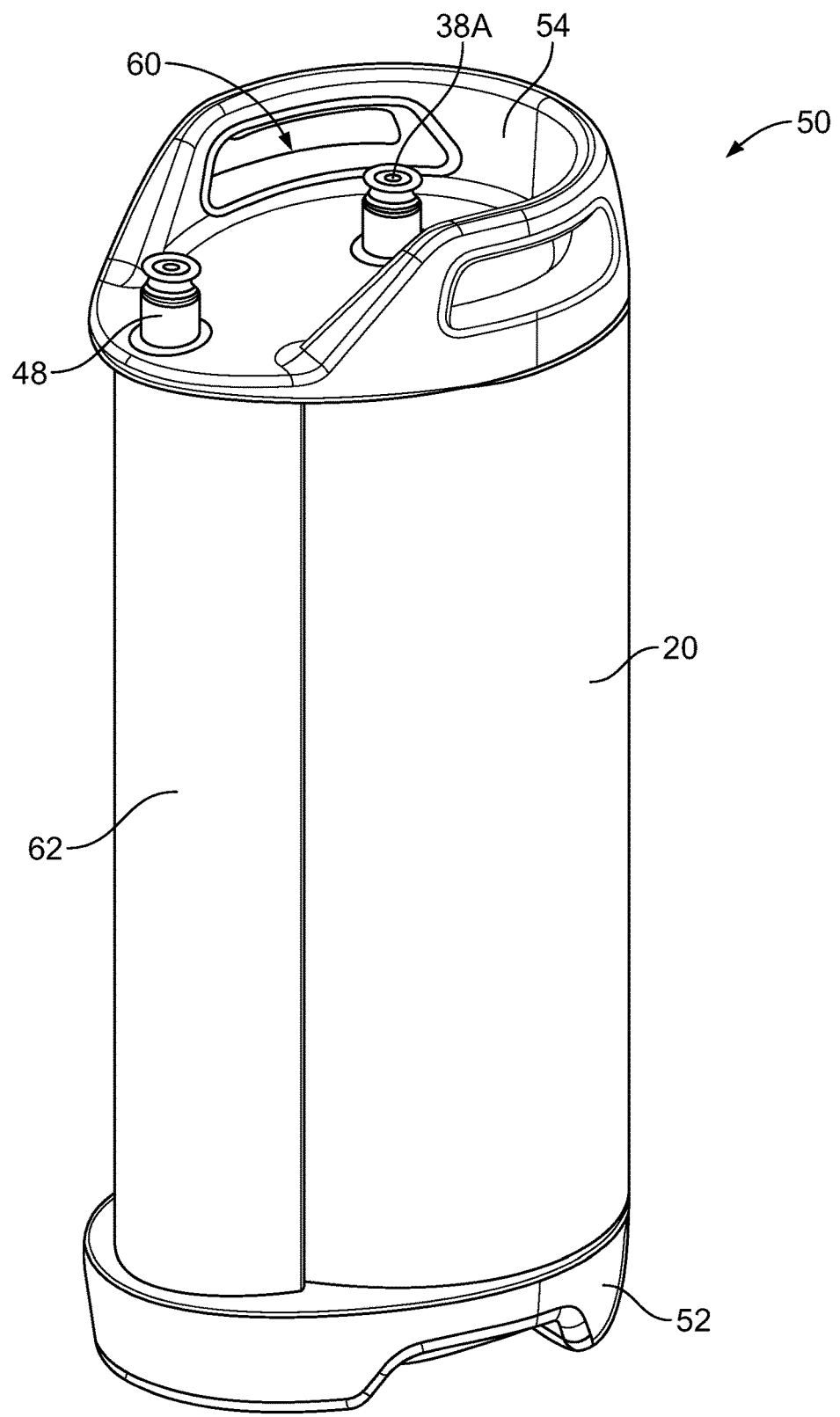
FIG. 1 is a schematic diagram of one of the chromatography columns described herein.

The sterilized chromatography columns described herein can be made of relatively inexpensive plastic materials and can thus be considered disposable, yet are specifically designed to be sufficiently robust for use, even multiple uses. The new methods of sterilization described herein provide desired Sterility Assurance Levels (SALs), thus making the chromatography columns far more useful than presently available chromatography columns, while maintaining suitable functionality of the packed medium as well as the required pressure rating and mechanical properties. Thus, the new sterilized, pre-packed, disposable columns are ready for use in an aseptic or sterile manufacturing process, e.g., a protein purification process. These performance results are surprising, as it is generally known that ionizing radiation can degrade materials including polypeptides through reactive oxygen species such as hydroxyl radicals or singlet oxygen.

Embodiments of the invention include compositions that comprise a packed bed of chromatography media in a column and appropriate connections for use in a protein purification system that is sterile and can be used in purification processes. The examples demonstrate materials for the chromatography columns that retain chromatography performance even after sterilization by gamma irradiation. The examples further demonstrate column packing medium of multiple solid support types such as silica and agarose, e.g., that are functionalized to achieve affinity based separations that maintain suitable performance of separations after gamma irradiation sufficient to attain sterility. Further examples demonstrate the column materials of construction are not adversely affected by gamma irradiation to increase extractable or leachable contaminants from the column materials. The examples also provide means of attaining the sterilized composition in a form suitable for use in biologics separations commonly used in the biopharmaceutical purification processes.

Sterilizing Chromatography Columns

The new sterilized chromatography columns are made of plastic as defined herein, and thus can be made entirely from widely available plastic/thermoplastics and/or composites (such as polypropylene (PP), polyethylene (PE), polyamides (such as various nylons), acetals, or glass-filled, metal-filled, or carbon-filled plastics, e.g., glass-fiber, steel-fiber, and carbon-fiber plastics) or elastomeric components, and are sterilized with gamma radiation to a desired SAL. Of course, these materials can potentially be damaged by gamma radiation of too high a dose. In addition, the packing media and functionalizing materials, e.g., binding agents, can also be damaged by inappropriate levels of radiation. Thus, it was surprising that pre-packed, disposable chromatography columns could be made that were sufficiently sterilized to meet SAL guidelines, while still maintaining sufficient functional performance of the column packing medium, column mechanical properties, and pressure ratings. Further, it was surprising that the irradiation causes no significant contaminants to be extracted by commonly used organic solvents or leached from the materials after use in standard aqueous buffers.

In general, the columns are packed with any of a variety of packing media with a silica, agarose, ceramic, or other polymeric backbones, which can be functionalized, e.g., with one or more types of affinity ligands or binding agents (e.g., Protein A ligands, such as recombinant native structure, or engineered functional domains), ionic interaction ligands, mixed mode ligands, and hydrophobic ligands. In general, the Protein A ligands can include the full-length wildtype *Staphylocuccus* protein A (SpA), a recombinant form of Protein A (e.g., as described in Peyser et al., U.S. Pat. No. 7,691,608, or monomeric or multimeric ligands that include any one, two, three, four, five, or more domains of SpA, e.g., selected from any one or a combination of domains A, B, C, D, E, or Protein Z (e.g., as described in Spector, U.S. Pat. No. 8,592,555 and Hall et al., U.S. Pat. No. 8,329,860). For example, a multimeric polypeptide can be made from three, four, five, or more domains, which can all the same or different. For example, a multimeric protein can include five SpA C domains to form a Penta C polypeptide.

Further details on the columns and packing media, and how to assemble certain embodiments of chromatography columns, are provided below.

Once a column is packed, the packing media are maintained hydrated for protective with a protective solution, which as described herein are designed to include certain components that include, for example, chemical groups such as thiol groups (for example cysteine) and hydroxyl groups on aliphatic carbons (for example ethanol). In addition, the protective solutions can contain other alcohols that contain compounds such as polyvinylpyrrolidone (PVP).

While aromatic compounds are sometimes found to be radiosensitizers and increase radiation damage, the present methods using an aromatic alcohol, benzyl alcohol, were found to be quite protective to the Protein A polypeptide immobilized on chromatography media. Thus, the functional performance of packing media as well as any functionalizing agents, e.g., binding agents or ligands as described herein, such as Protein A, can be preserved when irradiated in a protective solution containing a low percent (V/V), e.g., 1 to 25%, e.g., 1, 2, 3, 5, 7, 8, 10, 12, 15, 18, 20, 23, or 25%, of an alcohol, such as an aliphatic alcohol (e.g., ethyl and isopropyl), an aromatic alcohol (e.g., benzyl, tryptophol, tyrosol, and phenethyl alcohol (Phenylethanol)), or polyols, such as sugar alcohols (e.g., sorbitol and mannitol).

Once the column is filled with packing medium and protective solution, and the flow distributors are secured in the column tube, the entire pre-packed column is optionally enclosed within an airtight and watertight container, e.g., a bag, cylinder, or box of plastic, rubber, or other material that can be flexible or rigid, and that can be easily transported with the sterilized column inside. This container is designed to be sufficiently robust to permit transport without rupture, to maintain the sterilized pre-packed column under sterile conditions within the container. In some cases, the column remains sterilized without the addition of the container.

Once enclosed in the container, the entire container and pre-packed column inside are irradiated with a dose of gamma radiation to provide a desired SAL. The general concept of SALs is described, e.g., in "Guide to Irradiation and Sterilization Validation of Single-Use Bioprocess Systems," BioProcess Int'l, 10-22 (May 2008), which is incorporated herein by reference in its entirety. Gamma radiation dosage is measured in kilogray (kGy) units, which quantify the absorbed energy of radiation. One gray is the absorption of one joule of radiation energy by one kilogram of matter (one kGy=one joule/gram). Dosages of at least 8 kGy are generally adequate to eliminate low bioburden levels and provide a sterilization level of $10^{-3}$ organisms/unit. A level of $10^{-6}$ organisms/unit can be typically obtained using a dosage of at least 25 kGy. However, gamma radiation doses that are too high can destroy the functionality of the column packing media and even the columns themselves. Thus, the levels of gamma radiation for the pre-packed columns must be at least 8.0 kGy and can be up to about 35 kGy or more, e.g., the level of irradiation is selected from doses of between about 8 and 40 kGy, e.g., 8, 12, 15, 17.5, 20, 22.5, 25, 27.5, 30, 32.5, 33, 35, 38, and 40 kGy.

Such radiation doses can be achieved with high-energy photons, e.g., that are emitted from an isotope source (e.g., Cobalt 60) that produce ionization (electron disruptions) throughout the irradiated product. For example, the container in which a packed column is sealed can be placed into a chamber in which it is exposed to the radiation source for a sufficient length of time to achieve the desired SAL. Thereafter, the column, still within the airtight container, is removed from the source of radiation, and can be transported within the sealed container, thereby maintaining the sterility of the column. The sterility of the column flow path can be maintained outside the box or bag container by use of sealed tubing and flow paths that provide sterile connecting ports to other equipment used in the manufacturing process. Sterility within the column is maintained over a long time use, e.g., one month, two months, or more, depending in part on the nature of the container used to store the sterilized column. The examples below demonstrate that upon gamma irradiation at various levels, there were minimal changes in column physical properties, and the mechanical and structural properties are similar to those of a non-irradiated column. Other examples demonstrate that upon gamma irradiation, the functional performances of the chromatography media are changed only very slightly, and that the chromatography media still perform in a manner suitable for use in biologics manufacturing.

Chromatography Columns and Packing Media

The chromatography columns described herein consist primarily of a column tube and a pair of flow distributors (or one flow distributor and one end cap). The flow distributors include a cylindrical disc and one or more inlet/outlet pipes that enable liquids to flow into and through the disc. In addition, the flow distributors can include a bed support, screen, and/or filter that are attached to the packing medium side of the flow distributor disc.

The flow path of the flow distributors can be designed according to standard practices and known designs, and the flow distributors themselves can be made, for example, of the same or a similar plastic material as the tubes, but can also be made of metal, ceramics, and other materials that are inert to the liquids and reagents that are to be flowed through the columns.

The tubes are hollow, typically round, cylinders that permit a fluid (e.g., a liquid) to flow from a first end (e.g., an upper end) to a second end (e.g., a lower end). The inner diameter of the tubes are sized and configured to receive the flow distributors for delivering fluid to and removing fluid from the tube. Based on various chromatography column performance specifications, the tubes can be made in a variety of different sizes and configurations. In some embodiments, the tubes are sized and configured to maintain structural integrity under the induced internal operating pressures of the system while being able to withstand internal pressures up to as much as about 185 psi (e.g., about 20, 30, 40, 50, or 60 psi). In some embodiments, the tubes are typically cylindrical and have an inner diameter that is about 5 cm to about 100 cm and a length that is about 5 to about 90 cm.

In general, the overall induced hoop tension of the tube, based on a variety of factors, can vary based on an end user's specification, such as expected internal pressure to which the chromatography column will be subjected. The details of the methods of assembling and packing the columns are described in US 2013/0193052 (which corresponds to WO 2013/116367), which are incorporated herein by reference in their entirety.

Figure 4A:
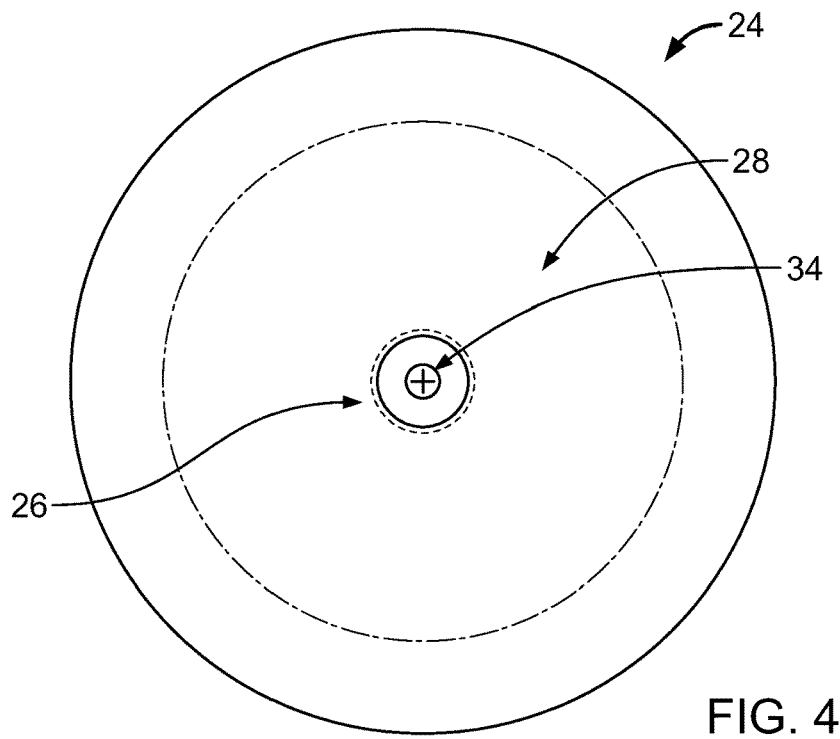
FIGS. 4a-4c are schematic diagrams of a top, front, and bottom views, respectively, of one example of a flow distributor that can be used in the new chromatography columns described herein.
Figure 4B:
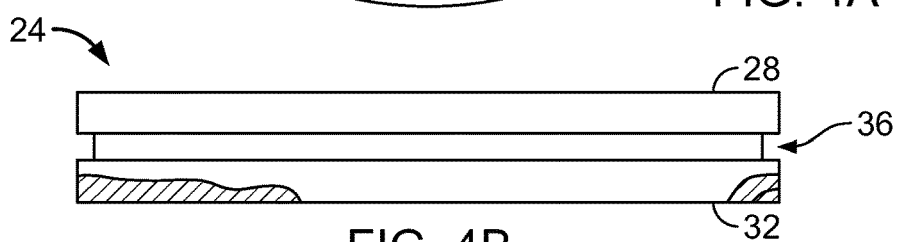
Figure 4C:
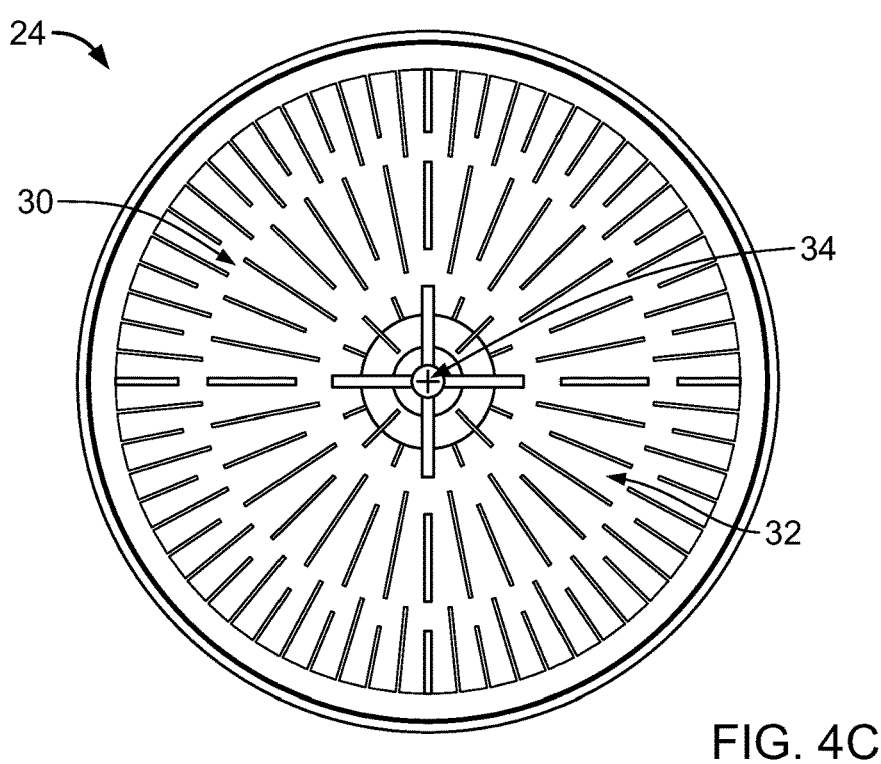

FIGS. 4a-4c illustrate that in some implementations a flow distributor 24 is a disc-like member having a fitting hole 26 formed at a central region along a first side 28 and a system of multiple grooves and channels 30 formed along a second side 32. The fitting hole 26 is a blind hole that is sized and configured to receive a fitting. The fitting hole 26 includes one or more features to receive the fitting. In one specific implementation, the fitting hole 26 is threaded to receive a threaded fitting (e.g., an M30×3.5 threaded fitting). In some embodiments, the fitting is connected to the flow distributor 24 in various other ways, such as adhesives, welding, bayonet or luer connections, or other sufficient connection techniques. In some embodiments, the fitting is manufactured as an integral component of the flow distributor 24. The flow distributor 24 also includes a fluid passage 34 to hydraulically connect the fitting hole 26 to the second side 32 of the flow distributor 24 so fluid can pass between the second side 32 of the flow distributor 24 and a fitting inserted into the fitting hole 26.

The flow distributor 24 can be formed by any various manufacturing techniques, such as molding, casting, machining, or other methods, and can be obtained commercially. In some embodiments, a general shape of the flow distributor 24 is cast or molded and the grooves and channels 30 are machined from the general shape. To closely mate with the inner diameter of the tube, in some embodiments, an outer diameter of the flow distributor is formed using a lathe to ensure that the outer edge is round and to tolerance.

Figure 2A:
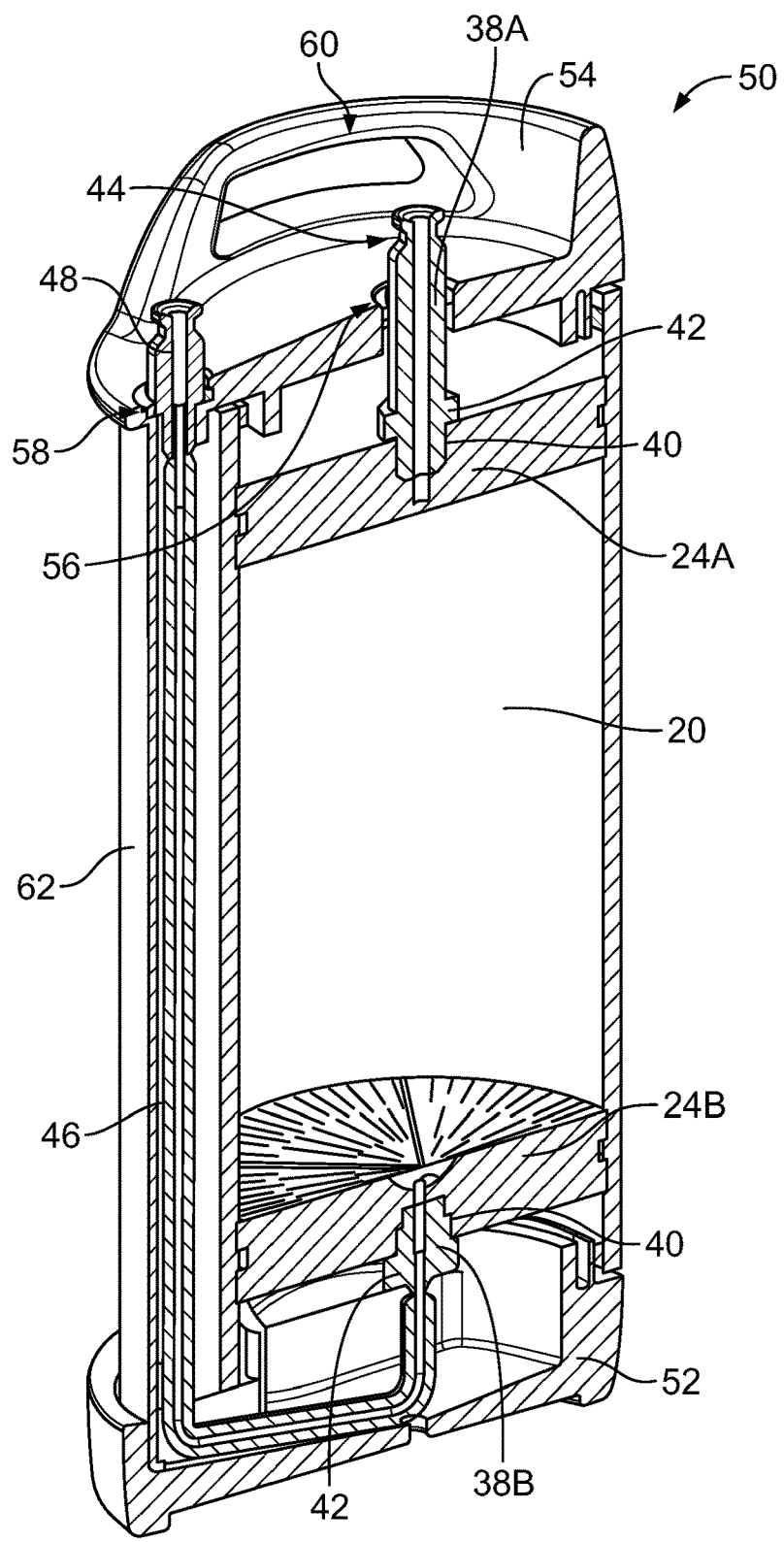
FIG. 2a is a schematic cross-section of the column of FIG. 1.
Figure 2B:
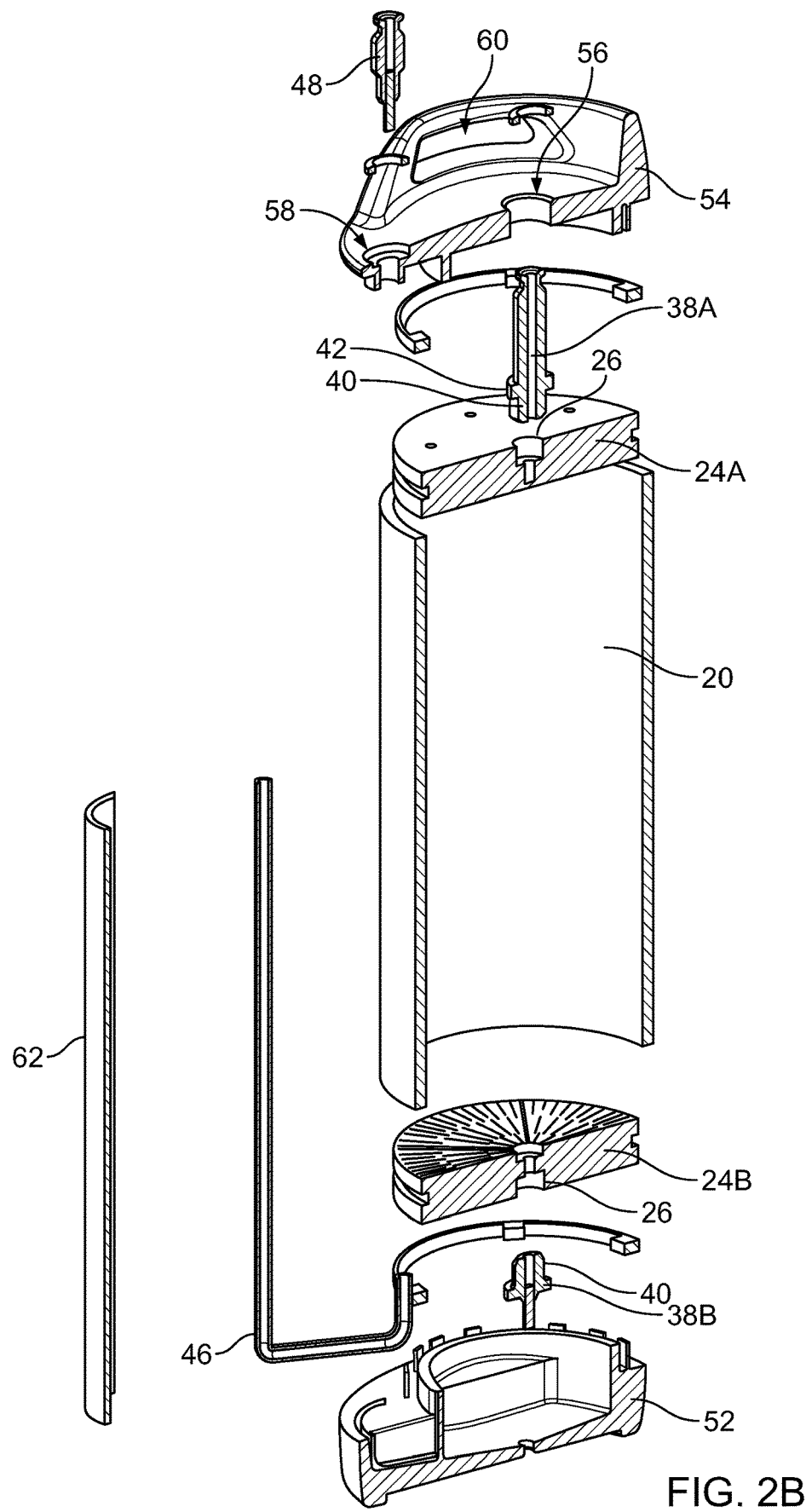
FIG. 2b is an exploded schematic cross-section of the column of FIG. 1.
Figure 3A:
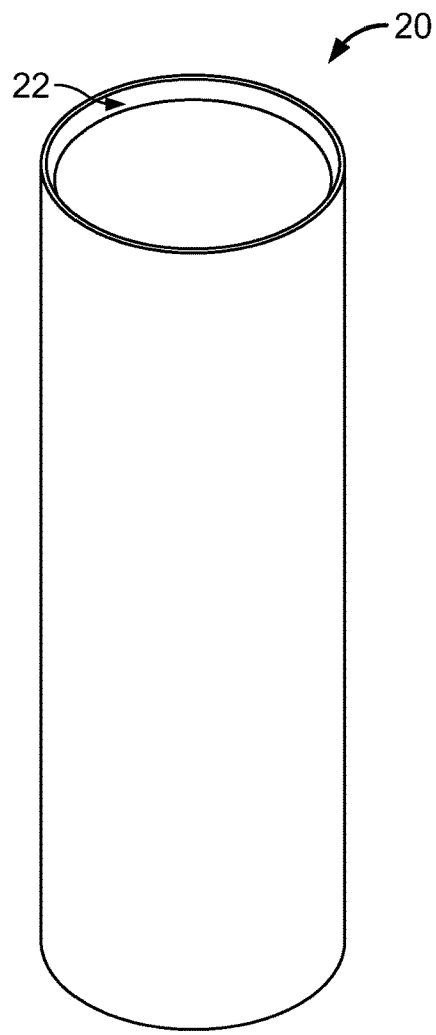
FIG. 3a is a schematic diagram of a column tube.
Figure 3B:
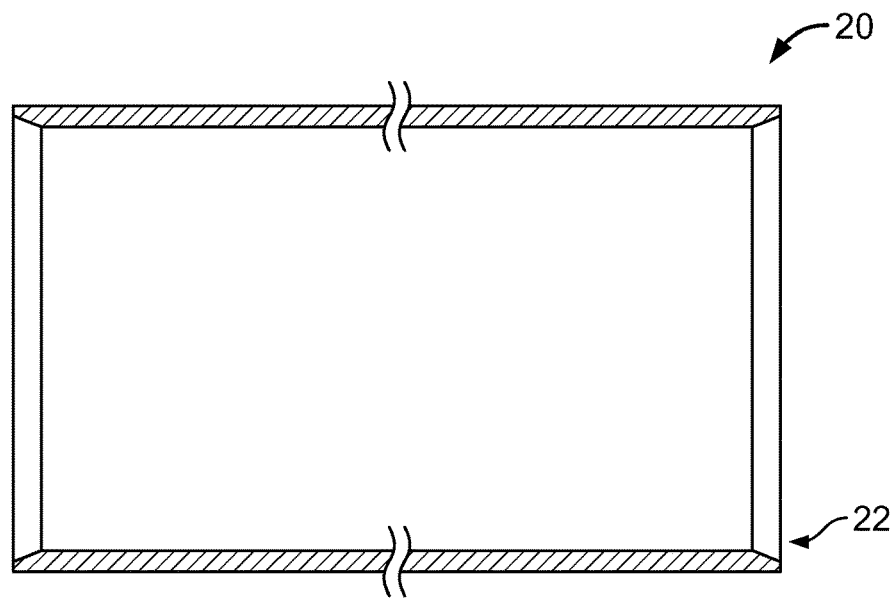
FIG. 3b is a schematic diagram of a column tube shown in cross-section.

The fittings are mechanical attachments that can be fastened or secured to the flow distributor to deliver fluid to or remove fluid from a flow distributor and the tube in which the flow distributor is arranged. To deliver fluid, the fittings have a fluid delivery hole formed through the fitting along its central axis. The fittings also include one or more features to be received in the fitting hole of the flow distributor to retain the fitting. As shown in FIGS. 1, 2a, and 2b, in this example, fittings 38 have a threaded end 40 (e.g., an M30×3.5 threaded end) to engage the fitting hole 26. The fittings 38 also have a nut portion 42 that can be gripped by a tool (e.g., a torque wrench) for turning and securing the fitting 38 within the fitting hole 26. In some embodiments, the fitting 28 includes other types of connection mechanisms, such as adhesives, welding, bayonet or luer connections, or other sufficient connection techniques.

Fittings 38 can have different additional features based on their installed location. For example, an inlet fitting 38a that is installed on a top flow distributor 24a can have a connection feature at an end of the fitting opposite the threaded end. The connection feature, such as a hose connection, permits hose or tubing to be connected to the fitting in an easy manner. In this example, the inlet fitting 24a defines a recess 44 that is sized and configured to be received in a hose fitting, such as a sanitary fitting (e.g., a tri-clamp connection or a cam lock) style hose fitting.

Alternatively, an outlet fitting 38b that is connected to the bottom flow distributor 24b can have a different style connection than the inlet fitting. In this example the outlet fitting 38b is secured to a hose 46 to hydraulically connect the outlet fitting 38b to a remote quick disconnect outlet fitting 48. The remote quick disconnect outlet fitting 48 can be mounted or arranged in a region that can be more conveniently accessed by a user than the outlet fitting 38b.

The chromatography column components (e.g., the tube 20, the flow distributors 24a, 24b, the fittings 38a, 38b, and other components) can be made from any of various structurally and chemically suitable plastic materials. For example, the components can be made of one or more thermoplastics (e.g., acrylonitrile butadiene styrene (ABS), acrylic (e.g., PMMA), polypropylene (PP), polyvinyl chloride (PVC), polytetrafluoroethylene (PTFE), other thermoplastics, or composites) and thermosetting plastics (e.g., epoxy resins, and fiber (e.g., glass or carbon) reinforced plastics). Material selection considerations include the specific mechanical properties of the materials and if the materials will withstand the induced internal operating pressures of the system.

Top and bottom flow distributors 24a, 24b are installed (e.g., press-fit) into the top and bottom of the tube 20 during the manufacturing and packing of the column. In some embodiments, the tube 20 and one or both of the flow distributors 24a, 24b are permanently bonded prior to insertion of the top flow distributor 24a and packing of the tube 20 with medium material. Following satisfactory testing of the column, the second, e.g., top, flow distributor 24a is permanently bonded in place.

Such permanent bonds cannot be readily separated other than by breaking the bond or the bonded items (e.g., the tube 20 and flow distributor 24a, 24b). At an upper end, an additional cap (e.g., the top cap) 54 can optionally be seated on and secured to the tube 20 and aligned so that the inlet fitting 38a installed on the flow distributor 24a at the top of the column passes through the inlet fitting hole 56 of the additional top end cap 54. Such optional top cap 54, which is primarily an aesthetic feature, can be secured to the tube 20 using various securement mechanisms, such as fasteners, adhesives, friction between the tube and the top cap, or other mechanisms.

The tubes of the chromatography columns described herein can be packed with any solid phase column packing medium that is used in column chromatography as specified by the end-user. This diversity of potential packing medium extends to both the composition of base particles as well as their functional chemistries (e.g., affinity, ion exchange, and hydrophobic interaction). Column packing medium can include a slurry of stationary phase particles added to an eluent solvent. Stationary phase particles can include agarose, silica gel ($SiO_2$), alumina ($Al_2O_3$), cellulose, and other suitable materials in various mesh sizes. Eluents can include one or more of various solvents, such as deionized water, ethanol or acetone.

Examples of packing media include, but are not limited to, agarose (e.g., Sepharose® Fast Flow and Capto™ from GE Health Care) controlled pore glass (ProSep® from Millipore), ceramic hydroxyapatite, polymethacrylate (e.g., ToyoPearl® media from Tosoh Bioscience), and other synthetic polymeric resins (e.g., Life Technologies' Poros™ media and Fractogel™ media from EMD).

Methods of Making Packed Chromatography Columns

One known characteristic of certain plastics/thermoplastics is their inherent compliance or ability to deform without fracturing with the application of force. The new chromatography columns are made using an assembly process that takes advantage of the "flow-ability," e.g., elasticity, of the plastics as defined by the induced hoop tension, used to make the column tube 20. The column tube 20 are made from extruded, cast, molded (injection, roto, or other), or machined plastic/thermoplastic or tape laid composite materials of specified internal and external dimensions. The designs and methods described herein for the flow distributors 24 include an outside diameter that is larger than the nominal internal diameter of the column tubes 20, described henceforth as the interference fit.

When used with cylindrical column tube 20, the flow distributors 24 must also be round, with as few (e.g., no) non-uniformities as possible on the outer surface, to ensure a uniform induced hoop tension and a sufficiently liquid-tight mating and sealing of the flow distributor 24 against the surface of the inner wall of the tube 20 when press fit into the tube 20. A sufficient degree of uniform roundness or circularity can readily be achieved by turning the flow distributor 24 on a lathe, but other methods of achieving this degree of uniform roundness are known to those skilled in the art.

The degree of acceptable interference-fit is determined by the mechanical properties, i.e., the elasticity or flow-ability, of the particular plastic/thermoplastic or composite components encompassing the tube 20 and flow distributor 24, and therefore, in the case of polypropylene, the thickness, of the tube 20 wall, but in all cases, the outer diameter of the flow distributor 24 exceeds the nominal inner diameter of the tube 20 to produce the required interference fit to assure satisfactory induced hoop tension when the flow distributor 24 is driven into the tube 20.

This assembly process provides unique advantages to the new chromatography columns. Traditional columns constructed of more dimensionally stable materials (steel, glass, etc.) are designed such that the flow distributor 24 is slightly smaller than the column tube, which is necessary to allow this component to be easily inserted and moved to the desired position within the column tube during assembly. An O-ring or similar sealing mechanism is employed around the flow distributor 24 to achieve a liquid-tight seal between the flow distributor 24 and the tube 20 wall. In these traditional designs, the combination of a flow distributor with smaller outer diameter than the tube inner diameter and the necessity to include an O-ring necessarily results in an area that is referred to as a "dead space" between the flow distributor 24 and the tube 20 wall up to the point at which the O-ring is seated. These "dead spaces" are difficult to expose to column flow and therefore pose a risk to column cleanability and resulting cleanliness. The interference fit design eliminates or greatly reduces the "dead space" of traditional columns thereby minimizing risk of carry-over contamination between column uses. The interference fit can, in some embodiments, also allow the elimination of O-rings altogether, thereby minimizing column complexity, cost, and risk to integrity due to seal failure. Another advantage of this feature is to reduce the exposure of a valuable product being purified by column chromatography to contaminants that may be released from such O-rings (typically elastomerics) that require costly and time consuming risk assessments in the form of studies of the extractables and leachables.

Figure 8:
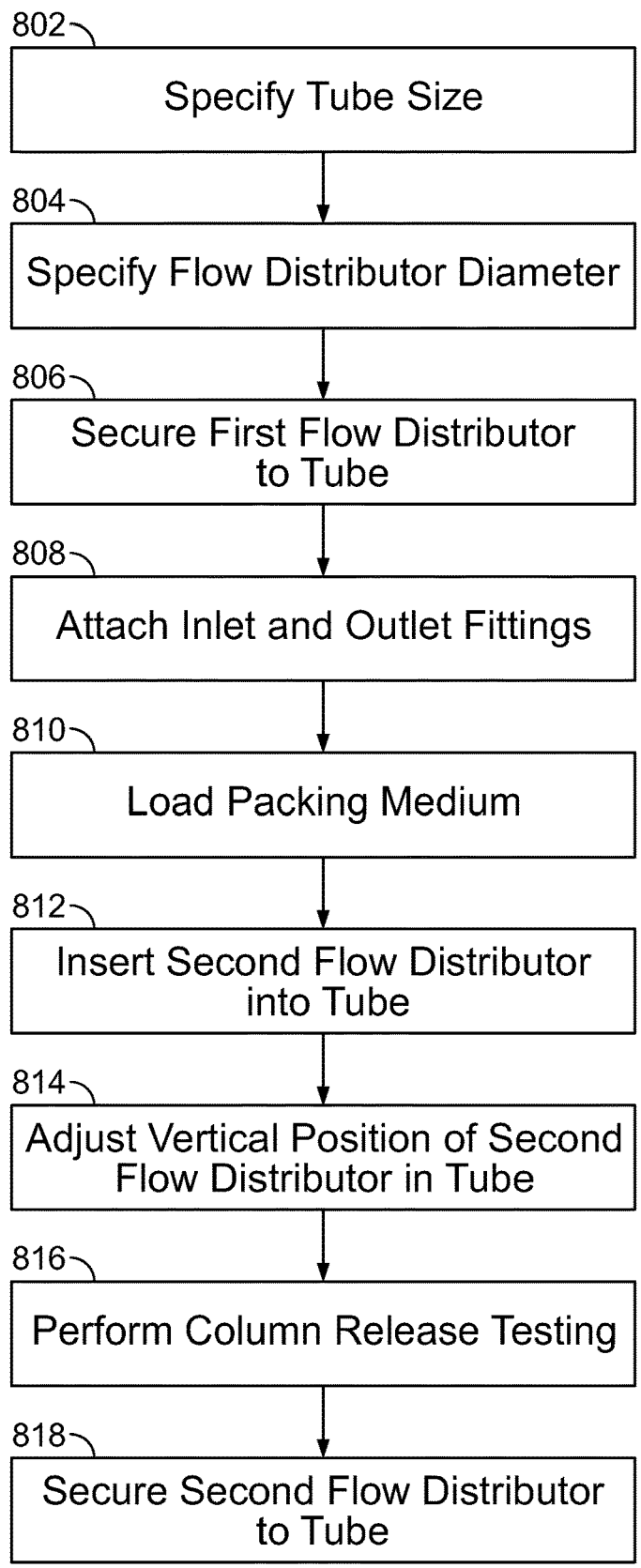
FIG. 8 is a flow chart of the basic steps in the manufacture of one of the chromatography columns described herein.

As shown in FIG. 8, the methods of making the new chromatography columns 50 include several steps.

First, specify a plastic column tube 20 that has the appropriate diameter and length to accommodate the volume of medium material that is desired for the final column (802), as well an appropriate elasticity, as described elsewhere herein. The length of the tube should be about twice the length or "bed height" of the medium material in the final column. The final length of the tube 20 can be about the same as the inner diameter, e.g., 200 and/or 199.90 mm inner diameter tube 20 might have a final length of about 150 to 250 mm, e.g., about 200 mm. The chamfer formed along the inner surface of each end of the tube is also selected. This chamfer is required to align and assist in inserting the flow distributors 24 to be driven into the interior of the column tube 20.

Second, an appropriately sized flow distributor 24 should be specified to have an outer diameter that is slightly larger, e.g., about 0.25%, 0.5 to about 1.0, 1.5, 2.0, 2.5, 3.0 or 3.5% larger than the inner diameter ("ID") of the tube (804). For example, for a polypropylene tube having an inner diameter of and/or 199.90 mm, the flow distributor 24 should have an outer diameter ("OD") greater than 201.90 mm, e.g., of between 202 and 204, 202.5, 203, 203.5, 204, 204.5, 205, 205.5 mm) The flow distributor 24 is designed to a specific nominal OD such that it will induce sufficient hoop tension in the tube 20 wall. When selecting the appropriate nominal OD account factors to consider include the physical properties of the materials of construction (e.g., coefficient of friction, Young's modulus, modulus of elasticity, and elongation at yield) in combination with the geometries including tolerances of both the column tube's ID and its wall thickness and the tolerance of the flow distributor 24 OD. The forces required to press-fit the assembly together can be theoretically determined (e.g., via advanced analytical tools, such as Finite Element Analysis) and, as an alternative, this assessment may be carried out by empirical studies with specific materials of construction.

In some embodiments, the flow distributors can be made of the same material as the tube, to ensure compatibility in use and to simplify the securing of the flow distributor to the interior wall of the tube, e.g., during welding.

Figure 5:
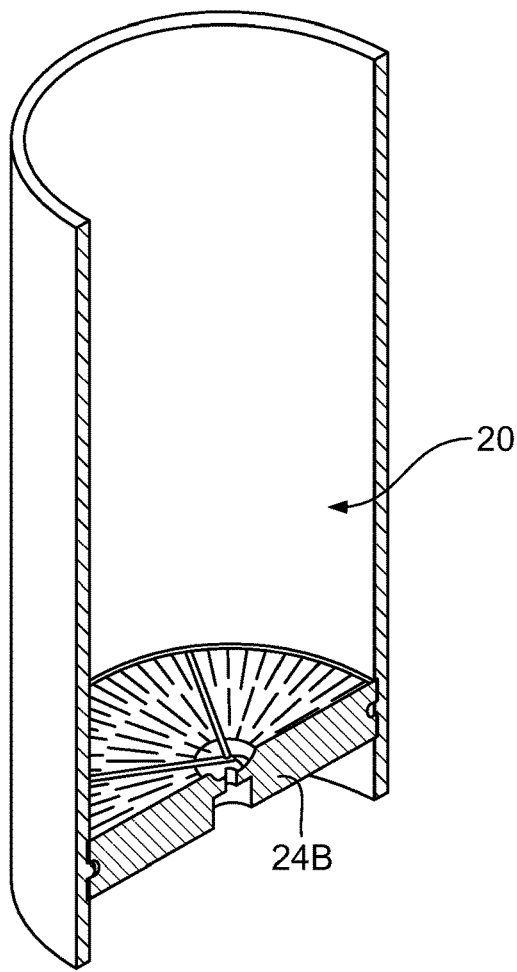
FIG. 5 is a schematic diagram of a flow distributor just after insertion into a column tube shown in cross-section.

Third, as shown in FIG. 5, a first, e.g., bottom, flow distributor 24b is secured to a first end, e.g., the bottom end, of the tube 20 (806). This can be done by any known means, or the interference fit methods described herein can be used to help avoid or reduce any dead space associated with the first flow distributor. For example, the first flow distributor 24b can be secured using metal clamps, threading cut into the tube 20 (either on the inner wall or on the outer wall) and flow distributor peripheral wall, adhesives, and various types of welding. The main point is that this first flow distributor 24b need not be moved once it is secured to the first end of the tube 20. In some embodiments, the first flow distributor 24b is formed as an integral part of the tube 20. For example, the first flow distributor can be molded as a feature of the tube 20 using known techniques.

If the interference fit method is used for the first, e.g., bottom, flow distributor, it can be initially held in place at the desired location by an induced hoop tension to provide an effective hydraulic seal at the required pressures, and then permanently secured at that location using any known means, including welding, screws, or adhesive. In particular, to establish an appropriate interference fit, the flow distributor 24 is aligned with the chamfered bottom end of the tube and then an axial force of about 1000 lbf to 10,000 lbf (e.g., 1000, 2000, 3000, 4000, 5000, 6000, 7000, 8000, 9000, or 10,000 lbf) is applied on the flow distributor 24 to drive it into the column tube 20, thereby expanding the inner diameter of the tube. For example, while the flow distributor 24 is inserted into the tube 20, both the tube 20 and the flow distributor 24 are plastically deforming to fit together, the magnitude of the tube 20 deformation is larger than the magnitude of the flow distributor 24 deformation.

The force required to drive the flow distributor into the tube depends on, amongst other factors, the angle of the chamfer formed into the tube, and other physical characteristics specific to the materials of construction (mentioned above) in combination with their geometric dimensions. For example, the axial force to drive the second flow distributor into the tube to establish the interference fit within the tube is a function of the interference fit, tube wall thickness, and specific mechanical properties of the tube and flow distributor materials. The force required to drive the flow distributor into either end of the tube can be measured by a load cell, or similar tensile testing instrument, and should be inspected during each assembly to assure adequate interference fit between the flow distributor and the tube wall. The axial force required to drive the flow distributor into the tube must be greater than and opposite to opposing forces resulting from adhesion and deformation friction forces between the tube wall and the flow distributor outer circumferential edges.

Equation 1 below describes the insertion force further.

$$F_{applied} > F_{friction,insertion} + F_{friction,deformation} = F_{friction,net} \quad (1)$$

where $F_{applied}$ is the axial force necessary to overcome the friction forces opposing the insertion of the flow distributor into the tube, $F_{friction,insertion}$ is the friction force due to adhesion between the flow distributor and tube wall materials, $F_{friction,deformation}$ is the friction force due to deformation of the flow distributor and/or tube wall, and $F_{friction,net}$ is the net frictional force. If necessary, one can differentiate the two opposing friction forces by applying a lubricant to remove the adhesion friction forces and subtracting the resulting axial force required to insert a flow distributor from the total axial force required to insert a flow distributor without the lubricant.

Alternatively, one can determine a minimum axial force to drive the flow distributor into the tube to produce a sufficient resulting induced hoop tension. This induced hoop tension acts as a radial force that holds the flow distributor at a specified location inside the tube. Considering well-known interference fit equations, an expression was derived to represent the induced hoop tension for all tube and flow distributor sizes.

The induced hoop tension can be related to a total radial force exerted by the tube wall on the walls of the flow distributor by multiplying it by the circumferential area of the flow distributor in contact with the tube wall. Equation 2 below explains this further.

$$\sigma_{hoop\ tension} = \frac{F_{radial}}{A_{contact,fd}} \quad (2)$$

where $F_{radial}$ is the radial force equally distributed around the tube walls acting radially inward to the flow distributor walls and $A_{contact,fd}$ is the area of the flow distributor in contact with the tube wall. It can further be scene that this radial force is directly related to the perpendicular friction force, $F_{friction,net}$, between the flow distributor and the inner wall of the tube. Thus, one can relate the force required to overcome the friction force, $F_{applied}$, to drive the flow distributor into the tube to an induced hoop tension, $\sigma_{hoop\ tension}$, that will hold the flow distributor at a desired location inside the tube. Equations 4, 5, and 6 below describe this relationship further.

$$F_{friction,net} = F_{radial}(\mu_{friction}) \quad (3)$$

$$F_{applied} \geq F_{friction,net} = \sigma_{hoop\ tension}(A_{contact,fd})(\mu_{friction}) \quad (4)$$

and $$\sigma_{hoop\ tension} \leq \frac{F_{applied}}{(A_{contact,fd})(\mu_{friction})} \quad (5)$$

where $\mu_{friction}$ is the friction coefficient between the flow distributor material and the tube wall material.

As a result of this correlation, as long as empirical testing can assure that a given induced hoop tension will provide a leak proof seal up to adequate factors of safety above the recommended maximum operating pressure, e.g., 2×, 3×, or 4×, one can assure, and check during assembly with a load cell or similar instrument, the adequate operating pressure of the column. It is important to note that dust, humidity, oxide films, surface finish, velocity of sliding, temperature, vibration, and extent of contamination to the column and flow distributor walls can contribute to variation in the value for the coefficient of friction, $\mu_{friction}$, thus affecting the recorded insertion force. In an attempt to reduce this error, it is recommended that all initial testing to determine the accurate coefficient of friction ($\mu_{friction}$) and subsequent applied load ($F_{applied}$) to achieve the required induced hoop tension be performed in a stable, repeatable manufacturing/laboratory environment, i.e., clean room. Ultimately, it is preferred that the facility has very little dust, low humidity, minimal UV light (that could affect the mechanical properties of the materials), minimal vibrations, constant temperatures (close to room temperature conditions), low extent of contamination, and a constant insertion velocity.

In addition, the following equation was used to determine the magnitude of the surface finish on the resulting interference fit and it was shown that the surface finish (for the materials in our case) are negligible on the overall interference fit.

$$\delta_{eff} = \delta_{int} - \Delta\delta \quad (6)$$

where $\delta_{eff}$ is the effective interference and $\Delta\delta$ is the Correction to the Measured Interference considering the surface finish of the inner tube wall and the circumferential surface of the flow distributor.

$$\Delta\delta = 0.1(2)(R_{z,tube} + R_{z,fd}) \quad (7)$$

where $R_{z,tube}$ is the surface finish of the inner wall of the tube and $R_{z,fd}$ is the surface finish of the outer wall of the flow distributor.

To guarantee sufficient induced hoop stress to contain this pressure, experiments can first be carried out to develop a relationship between the amount of interference between the flow distributor and the tube wall to prevent leaks up to a certain pressure. Equation (1) shows that the induced hoop tension is directly responsible for creating a leak-proof seal between the flow distributor and the tube wall. Three major variables, assuming constant tube and flow distributor materials, will contribute to the magnitude of the induced hoop tension: the interference fit $\delta_{int}$, outer diameter of the tube $D_{tube,o}$, and the outer diameter of the flow distributor $D_{fd}$. Once two of these values are chosen, varying the third variable will allow one to test several cases of applied force to insert the flow distributor $F_{applied}$ versus the internal pressure to leaking. Once an adequate internal pressure is attained without any leaks past the flow distributors, the value of applied force can be used to back calculate the induced hoop tension necessary to contain the desired pressures. Once the necessary induced hoop tension is found for a certain chromatography column size (tube internal diameter), the three major variables that contribute to the induced hoop tension can once again be modified to optimize the design as long as they ultimately attain the same final induced hoop tension value.

Figure 9A:
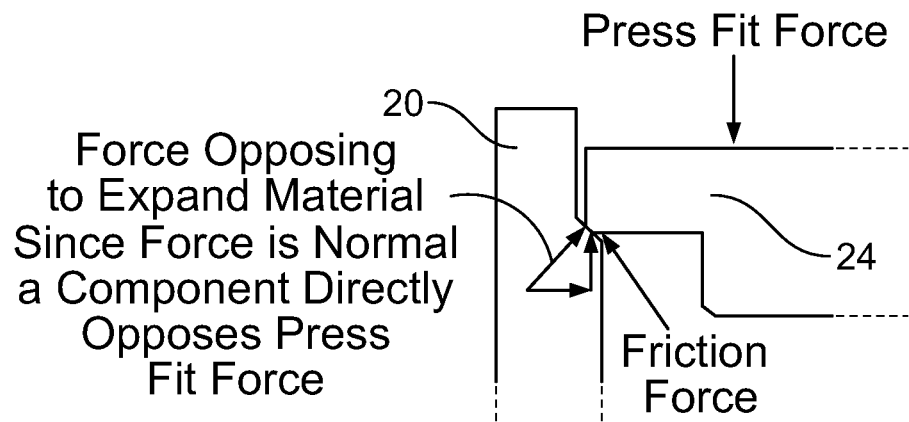
FIG. 9a is a schematic diagram of forces generated when pressing a flow distributor into a tube with a chamfered end to form an interference fit.
Figure 9B:
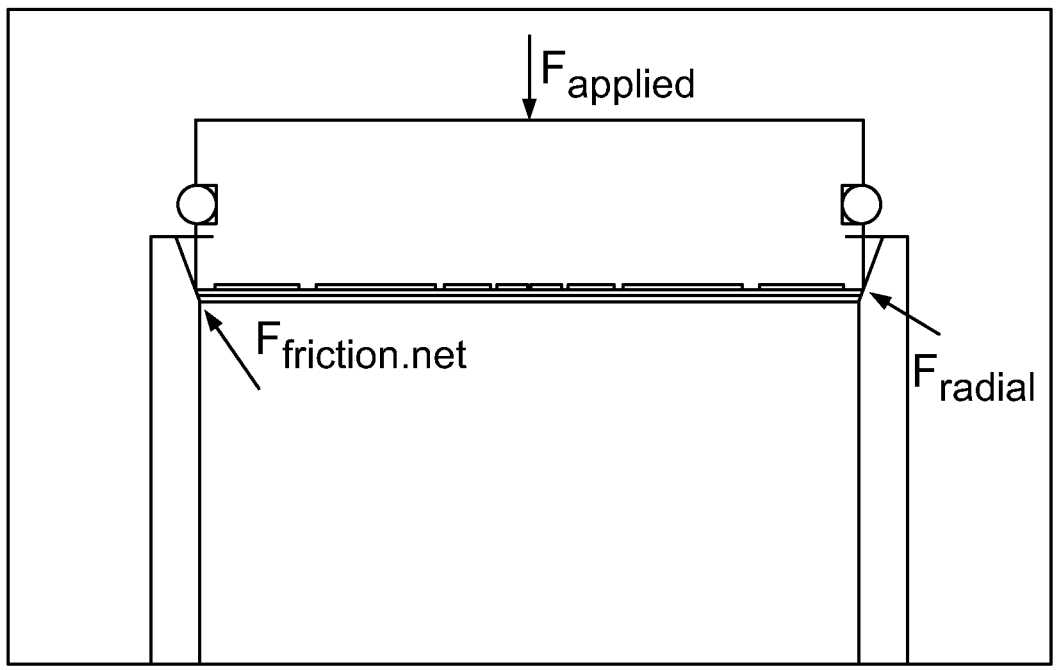
FIG. 9b is a schematic diagram of forces generated when pressing a flow distributor with an O-ring into a tube with a chamfered end to form an interference fit.

FIGS. 9a and 9b show schematic free body diagrams of the forces generated while a flow distributor 24 is initially driven into the tube 20 before it reaches a chamfer 22. As the flow distributor 24 first enters the tube 20, the tube 20 has not yet expanded. The interference between the flow distributor 24 and the tube 20 wall will force the tube 20 to enlarge and the flow distributor 24 to compress. Since the wall thickness of the tube 20 is smaller than the diameter and thickness of the flow distributor 24, the overall net force will result in expansion of the tube wall (note that the flow distributor 24 may correspondingly undergo a small amount of compression). For this to occur, the force in the axial direction must be large enough to overcome the force created due to the induced hoop tension. The axial force is from the linear actuator and the horizontal or radial force is from the induced hoop stress. The axial force is simply overcoming the frictional force. The frictional force is directly related to the value of the force from the induced hoop.

Figure 10A:
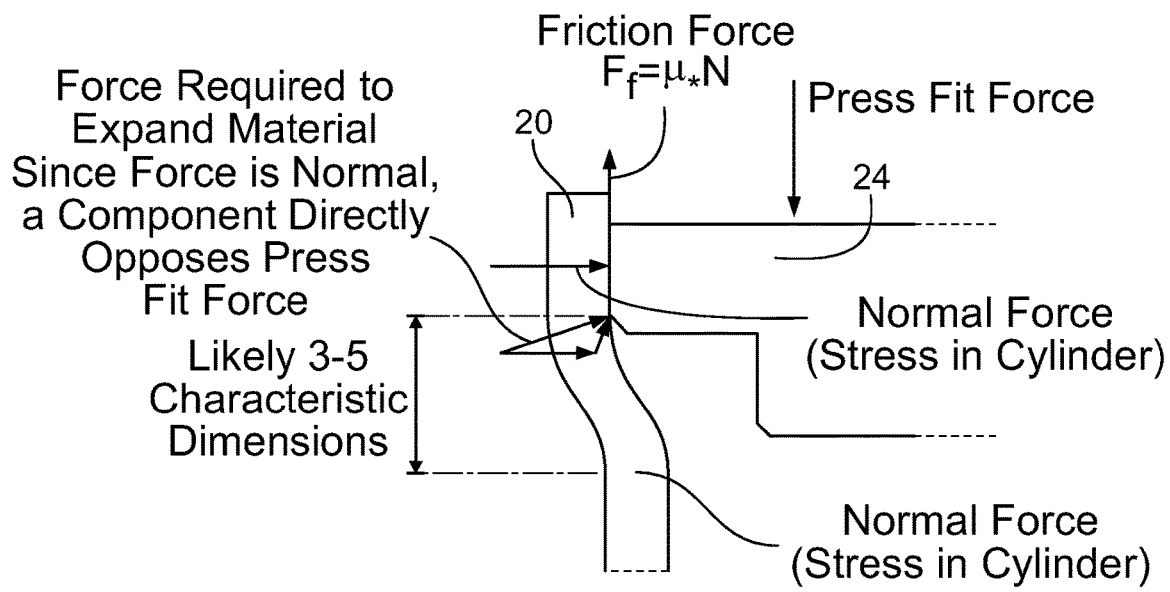
FIG. 10a is a schematic diagram of forces generated when pressing a flow distributor into a tube after an interference fit is formed.
Figure 10B:
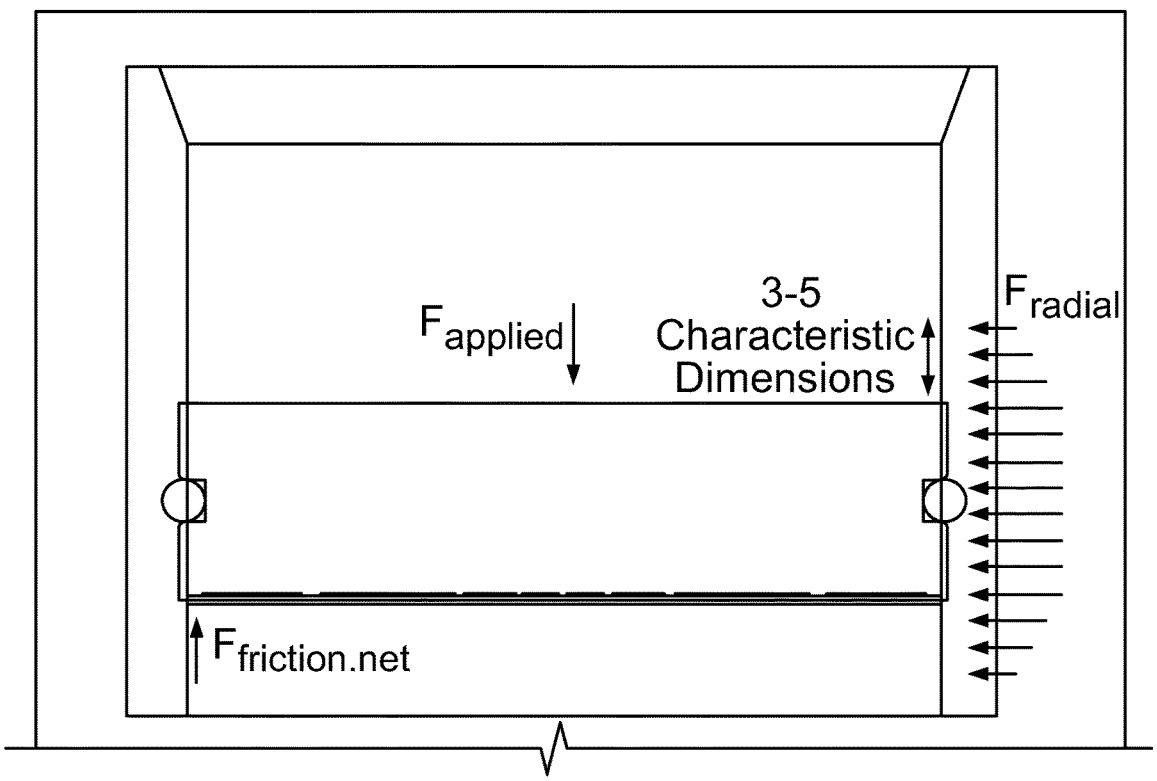
FIG. 10b is a schematic diagram of forces generated when pressing a flow distributor with an O-ring into a tube after an interference fit is formed.

FIGS. 10a and 10b show schematic, free body diagrams of the forces generated while the flow distributor 24 is driven along the axial length of the tube 20 after it passes the chamfer 22. Although some component of the axial force is contributing to expanding the tube 20, the stress is distributed 3-5 characteristic dimensions away from the initial contact point between the flow distributor 24 and the tube 20 and the tube 20 is already expanding in front of the flow distributor 24. Thus, as the flow distributor 24 is inserted axially further along the length of the tube 20, the axial force to push the flow distributor 24 is larger to overcome the higher induced hoop tension occurring not only at the point of contact with the flow distributor 24, but also 3-5 characteristic dimensions in front of the flow distributor 24. In some embodiments, the chamfer begins at the very end of the tube wall and e.g., can extend along the entire length of the tube.

Figure 11:
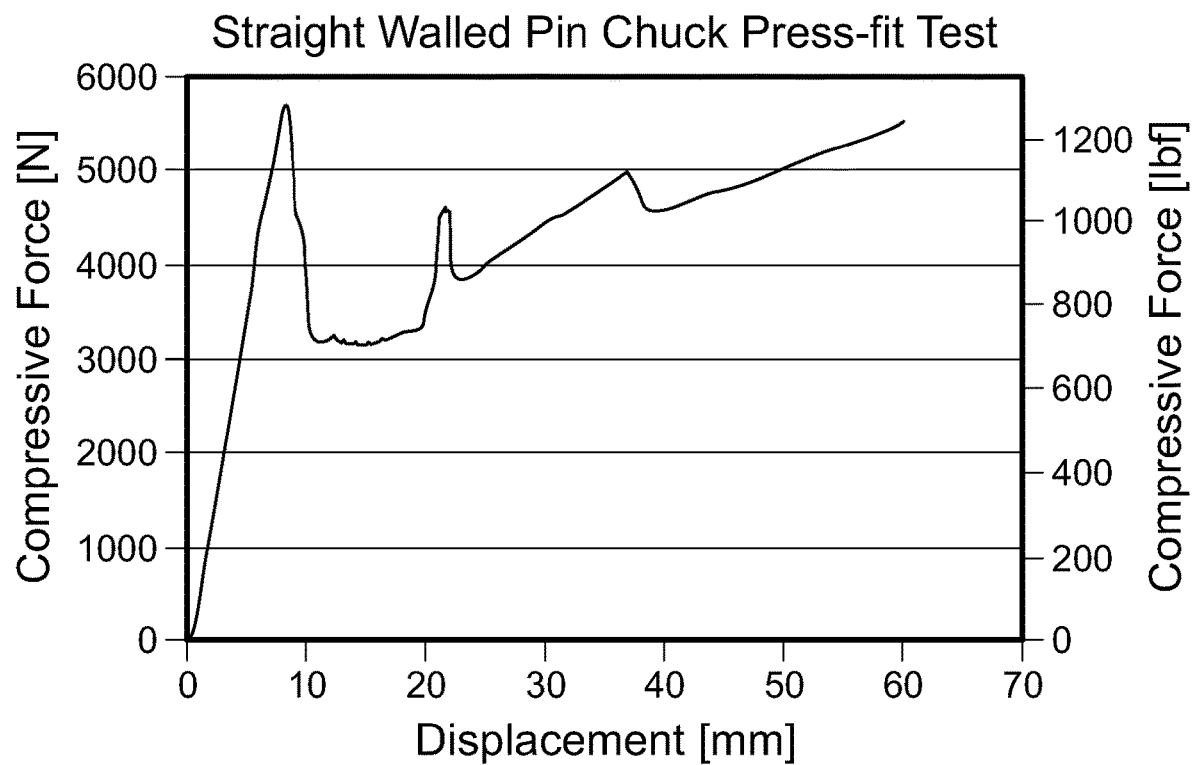
FIG. 11 is a plot illustrating an example of forces generated when pressing a flow distributor into a tube to form an interference fit.
Figure 12:
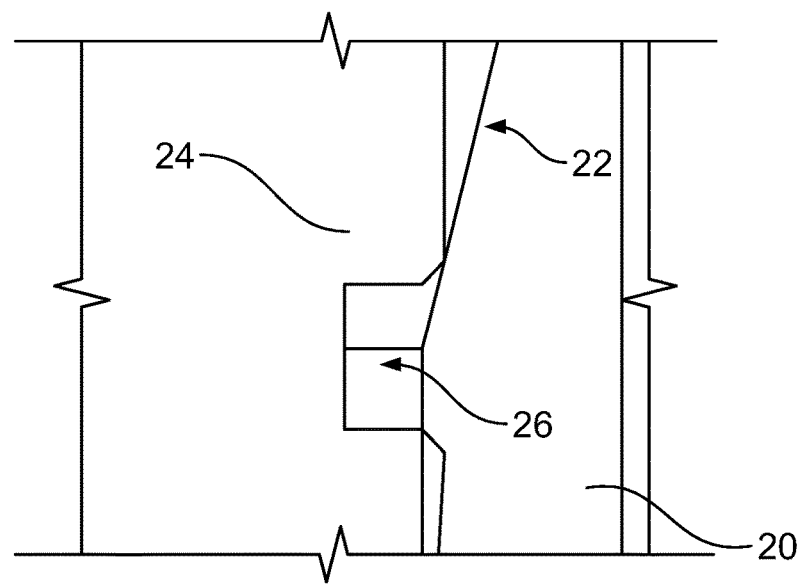
FIG. 12 is a schematic diagram of a flow distributor being driven into a tube.

FIG. 11 shows a chart illustrating the axial force required to press the flow distributor 24 into the tube 20 as the flow distributor 24 travels into the tube 20 in one embodiment. As shown, the force initially increases to a peak while a first portion of the flow distributor 24 enters and passes the beginning of the tube chamfer 22. Initially, the flow distributor 24 and tube wall are experiencing static friction and the force to overcome the static friction is greatest. Once the deformation of the flow distributor 24 and tube 20 wall give way to sliding of the flow distributor 24 into the tube 20, the force required to continue pressing the flow distributor 24 into the tube drops since it is experiencing dynamic friction. Dynamic friction is significantly less than static friction to overcome. Two additional peaks are also present in this graph. The first peak at about 21 mm corresponds to when a bottom of the chamfer 22 is in a fitting hole 26 of the flow distributor 24 (shown in FIG. 12). The second peak corresponds to the point at which the entire flow distributor 24 is engaged in the region of the tube 20 beyond the chamfer. As shown, in this example, the maximum axial force is about 1200-1300 lbf.

For certain embodiments, the seal can be improved by the use of an O-ring arranged within a fitting hole 26 in the outer wall of the flow distributor 24. In certain embodiments, the press-fit or interference fit is sufficient to hold the flow distributor in place, but in other embodiments, a more permanent bond is desired.

Once the flow distributor 24 has been driven about 1 to 10 cm, e.g., 6.0, 6.5, 7.0, 7.5, 8.0, or 8.5 cm, into the first, e.g., bottom, end of the tube, the flow distributor 24 can be permanently secured in place, for example by welding, e.g., if the flow distributor 24 and tube are made of the same or sufficiently similar materials. Various welding techniques can be employed to form the weld between flow distributor and column tube including, but not limited to, hot tool welding, hot gas welding (e.g., at 420° C.), ultrasonic, extrusion, laser, conductive, high frequency, etc. If the two pieces are made of different materials, they can be connected using mechanical clamps, such as metal hose clamps, applied externally to compress the tube and apply a force that will anchor the flow distributor within the tube at that location, or by adhesives or by mechanical fasteners that pass through the tube wall and into the flow distributor.

Fourth, the inlet and outlet fittings 38a, 38b are attached to the first (e.g., bottom) and second (e.g., top) flow distributors 24a, 24b (808). The inlet and outlet fittings 38a, 38b have threaded regions 40 that are screwed into threaded fitting holes 26 in top and bottom flow distributors 24a, 24b. A recess (e.g., an O-ring gland) can be formed either at a bottom end of the each fitting (i.e., an end that mates with a flow distributor) or in a terminal end of the threaded fitting hole 26 of the flow distributor. In this example, an O-ring is arranged between the fittings 38 and the flow distributors 24 to form a seal (e.g., a liquid-tight seal) between the fittings 38 and the flow distributors when they are threaded together. A torque wrench can be used to ensure adequate compression of the O-ring to create sufficient seal at this interface.

Next, the packing medium in the form of a liquid slurry is loaded into the column tube 20 in the space (chamber) above the bottom flow distributor 24b (810).

Figure 6:
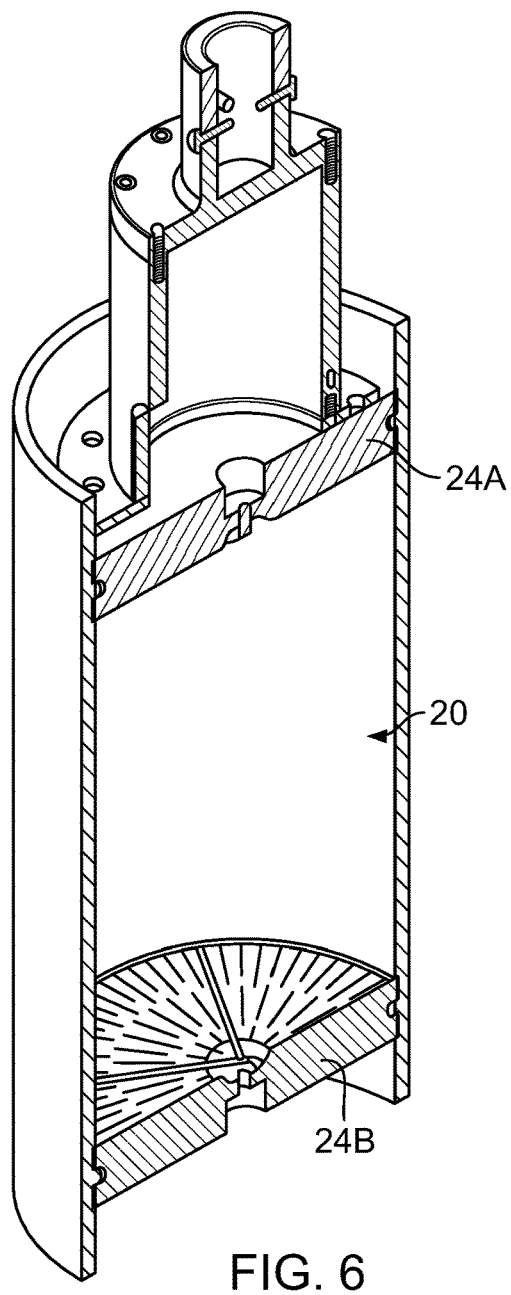
FIG. 6 is a schematic diagram of a column tube within a press used to apply axial force to a top flow distributor to drive it into the column tube to provide a tight interference fit shown in cross-section.
Figure 7:
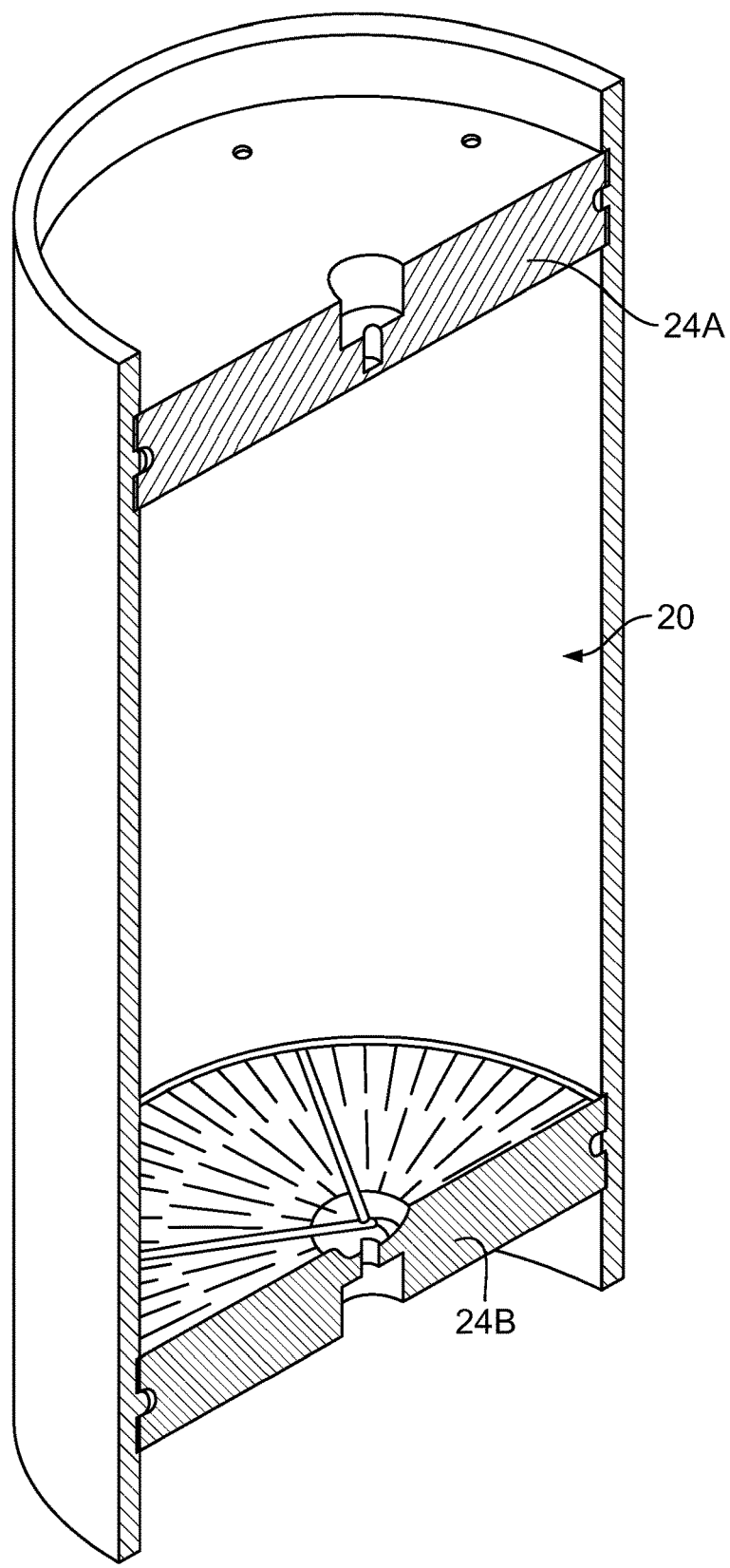
FIG. 7 is a schematic diagram of a chromatography column after the top flow distributor has been welded in place.

Next, as shown in FIGS. 6 and 7, once the second, e.g., top, flow distributor 24a is plumbed with tubing (and optionally already connected to a liquid source) it is inserted into the tube 20 in much the same way as the first flow distributor 24b is inserted when using the interference fit method (812). It is important that the interference fit method is used for the second flow distributor, because the initial location to which this second (e.g., top) flow distributor 24a is driven into the tube 20 should not be immediately fixed, because it may be desirable to readjust the initial position of the second flow distributor following testing. Thus, the interference fit method is used, so that the second, e.g., top, flow distributor 24a can be moved internally within the tube 20 to make final adjustments. It is also important that the interference fit be designed and implemented such that it ensures a liquid-tight seal at the pressures used during testing of the column.

At this point, the packing medium can be actively settled into a packed bed using a method suitable for the particular medium, for example, flow with an appropriately formulated solution ("mobile phase" or "packing buffer") or suction applied from the column outlet fitting 38b, or any other suitable known techniques or methods. The second, e.g., top, flow distributor can be driven further into the tube by applying an additional axial force to the flow distributor until it contacts the packing medium and may compress the packing medium to reach a desired position. Such compression can range from none at all to 30% or more of the packed bed height depending on the nature of the packing medium. The performance of the column as measured by HETP (Height Equivalent to a Theoretical Plate) testing and asymmetry analysis will be a function, in part, of the compression of the bed. If appropriate, it is also possible to move the inserted flow distributor 24a out towards the end of the tube to reduce bed compression. This is done using hydrostatic pressure by applying a force to the liquid inside the chamber created between the first and second flow distributors. Since the first flow distributor 24B is permanently secured, the second flow distributor 24A, which is secured using a press fit, will move once a force sufficient to overcome the press fit is exerted against it by the liquid within the column tube.

Next, suitability of the column packing medium can be tested by a pulse injection of an un-retained and readily detectable test article (e.g., acetone via UV monitoring or sodium chloride via conductivity monitoring) (818). Based on the outcome of the packing test, the top flow distributor 24a can travel down (e.g., can be driven) further into the packed bed and the packing test can be repeated. If the top flow distributor is moved too far into the tube, which can result in over compressing the packed bed, liquid can be forced into the chamber through the inlet fitting with the outlet fitting sealed shut thereby using hydraulic force to move the top flow distributor 24a back towards the top end of the tube and reducing compression of the packed bed. Once suitability of column packing is determined, the column can then be sanitized and/or flushed with a bacteriostatic protective solution per end-user specifications.

When the second, e.g., top, flow distributor 24a is properly positioned, it can be permanently secured, such as by welding or other means as noted above for securing the first flow distributor (818). In some embodiments, the interference fit may suffice to secure the top (or second) flow distributor 24a to the inner wall of the tube 20.

In some embodiments, the packed final chromatography column can then be fitted with a top cap, a base, and/or a side guard. The chromatography column can then undergo final sterilization and be used or packaged for shipping.

Methods of Use

The systems and methods described herein provide end-users with disposable, pre-packed, pre-qualified, and sterile chromatography columns that are comparable in performance to other chromatography columns that typically exist in a durable hardware installation requiring significant capital expenditure. The new sterilized columns are used in the same manner as other known chromatography columns, but given the disposability and sterility, the new columns are especially useful for separating and purifying reagents that are toxic or otherwise hazardous, e.g., viruses, pathogens, and toxins. Furthermore, these sterile columns can be used without fear of contamination that often occurs when columns are reused and cleaned ineffectively. For example, these sterilized columns can be used in sterile continuous processes and in multi-product facilities where high levels of microbial control are required.

The new sterile columns can be used in disposable systems and in multi-column-chromatography systems. The new sterile columns can also be connected to sterile systems via sterile connections.

In some uses, the columns can be pre-packed with various affinity capture media with two or more different SpA molecules.

EXAMPLES

The invention is further described in the following examples, which do not limit the scope of the invention described in the claims.

Example 1—Impact of Gamma Radiation on Pressure Tolerance

The purpose of this example was to determine the impact of the new sterilization methods described herein on a plastic chromatography column and its parts. This test involved irradiation of an assembled chromatography column that did not contain any packing medium, as well as irradiation of chromatography column parts to test the impact of gamma radiation on pressure tolerance of each component.

Column Materials
OPUS™ chromatography column (Repligen Corporation)
14 cm flow distributor
14 cm bed support—polypropylene mesh
14 cm flow distributor O-ring
Port O-ring (small O-ring)
Inlet port
Port clamp
Port plug
14 cm extruded polypropylene tube
Methods Chromatography column components were gamma irradiated at a dose between 15-40 kGy, with a desired target of 25 kGy by a sterilization contracting company, Steris Corporation, which provides contract sterilization services under their Isomedix Services business (Northborough, Mass.). The actual dose delivered was between 21.3-25.3 kGy. Steris Corp. uses high-energy photons emitted from an isotope source (Cobalt 60) to produce ionization (electron disruptions) throughout the pre-packed columns. In living cells, these disruptions result in damage to the DNA and other cellular structures. These photon-induced changes at the molecular level cause the death of the organism or render the organism incapable of reproduction, thus providing the desired sterilization.

For testing after irradiation, the column was attached to a pressure tank filled with water. The pressure tank can be pressurized using an external inert gas tank to up to 100 psi (7 bar). The column was first filled with water, and then subjected to increased pressure. A pressure gauge was attached to the inlet of the column to monitor the pressure increase during the test.

Results

A new chromatography column, non-irradiated, is rated to a maximum pressure of 4 bar. The column that was irradiated did not have the top adaptor welded, therefore it was expected to withstand a maximum pressure of less than 4 bar.

The top flow adaptor did not move until the pressure reached 5.5 bar. At 5.5 bar, the top flow adaptor started to move up slowly, until it could be removed completely from the column. This test demonstrates that the irradiated column has an equivalent pressure tolerance as a non-irradiated column.

Example 2—Impact of Gamma Radiation on Leachables and Extractables

The purpose of this example was to determine compatibility of the materials of chromatography columns with sterilization by gamma irradiation. In this example, the impact of gamma radiation on leachables and extractables from the column parts is determined.

Column Materials
OPUS™ chromatography column (Repligen Corporation)
14 cm flow distributor—machined molded polypropylene
14 cm bed support—polypropylene mesh
14 cm flow distributor O-ring—platinum cured silicone
Port O-ring (small O-ring)—platinum cured silicone
Inlet port—machined polypropylene
14 cm extruded polypropylene tube
Methods OPUS™ Chromatography column components were gamma irradiated between 15-40 kGy, with a desired target of 25 kGy by STERIS Isomedix (Northborough, Mass.) as described above in Example 1. The actual dose delivered was between 21.3-25.3 kGy.

Column materials, both irradiated and non-irradiated, were soaked in 20% ethanol and water respectively for 72 hours, at 37° C. At the end of the incubation time the supernatant was analyzed by reverse phase HPLC.

The HPLC method used for detecting leachables and extractables:
HPLC Column YMC C18-3 um, 12 nm
Buffer A: 0.1% TFA in Water
Buffer B: 0.1% TFA in Acetonitrile
Flow 1 mL/min

TABLE 1

| HPLC method for detecting leachables and extractables | |
|---|---|
| Time | % A |
| 0.00 | 5.0 |
| 45.00 | 50.0 |

TABLE 1-continued

HPLC method for detecting leachables and extractables

| Time | % A |
|---|---|
| 60.00 | 80.0 |
| 65.00 | 80.0 |
| 68.00 | 5.0 |
| 75.00 | 5.0 |

Results

Referring to FIGS. 14A-J, in 20% ethanol there are slightly higher levels of leachables and extractables than in water for both non-irradiated and irradiated column parts. The graphs show there are no significant leachables and extractables that become present after the plastics have been irradiated. The variability seen between samples is not statistically significant.

In 20% ethanol, all the column parts tested showed lower levels of extractables post irradiation than non-irradiated parts. In water, the column body had slightly higher levels of extractables post irradiation, but the difference was not statistically significant. The bed support showed higher levels of extractables in water post irradiation. However, the overall change was minor. Some compound peaks decreased, or completely disappeared in the irradiated samples, possibly due to cross-linking from the gamma irradiation.

Example 3—Impact of Gamma Radiation on Physical Appearance

The purpose of this example was to test the impact of gamma irradiation on the physical appearance of the assembled chromatography columns.

Column Materials
OPUS™ chromatography column (Repligen Corporation)
14 cm flow distributor—machined molded polypropylene
14 cm bed support—polypropylene mesh
14 cm flow distributor O-ring—platinum cured silicone
Port O-ring (small O-ring)—platinum cured silicone
Inlet port—machined polypropylene
Port clamp
Port plug
14 cm extruded polypropylene tube
Methods An assembled empty OPUS™ chromatography column was gamma irradiated between 15-40 kGy with a desired target of 25 kGy by STERIS Isomedix (Northborough, Mass.) as described in Example 1. The actual dose delivered was between 21.3-25.3 kGy.

Results

Figure 13:
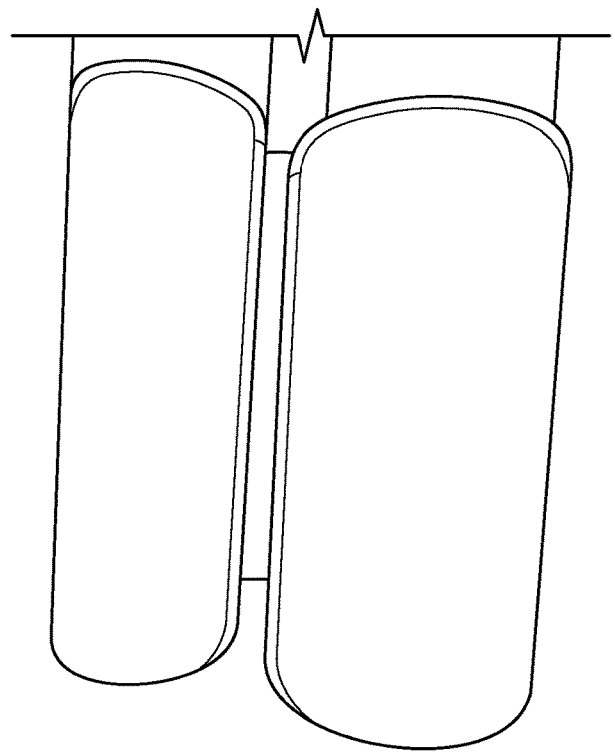
FIG. 13 is an illustration of the physical appearance of gamma irradiated polypropylene and non-irradiated polypropylene.
Figure 14A:
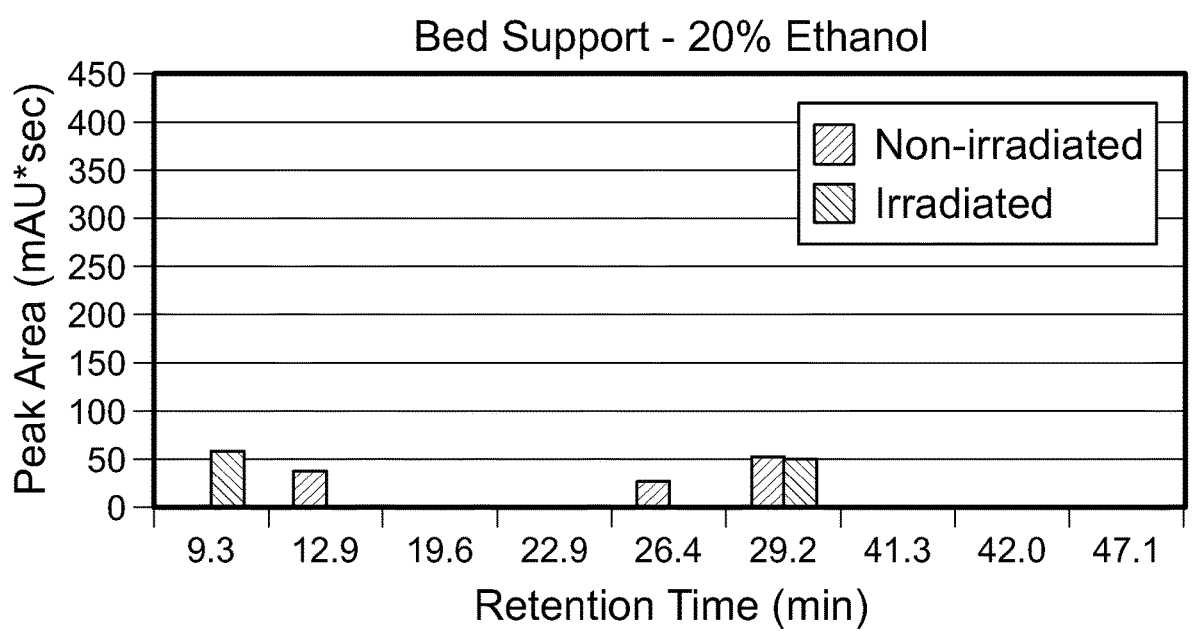
FIGS. 14A-J are plots illustrating the retention times and peak area for non-irradiated and irradiated components after exposure to water and ethanol.
Figure 14B:
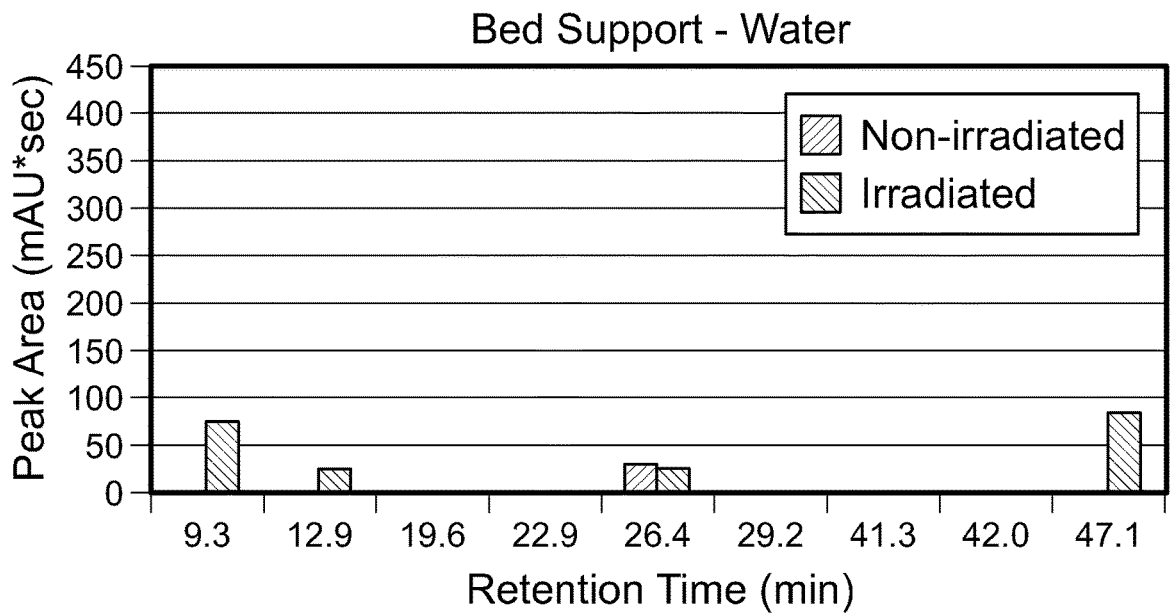
Figure 14C:
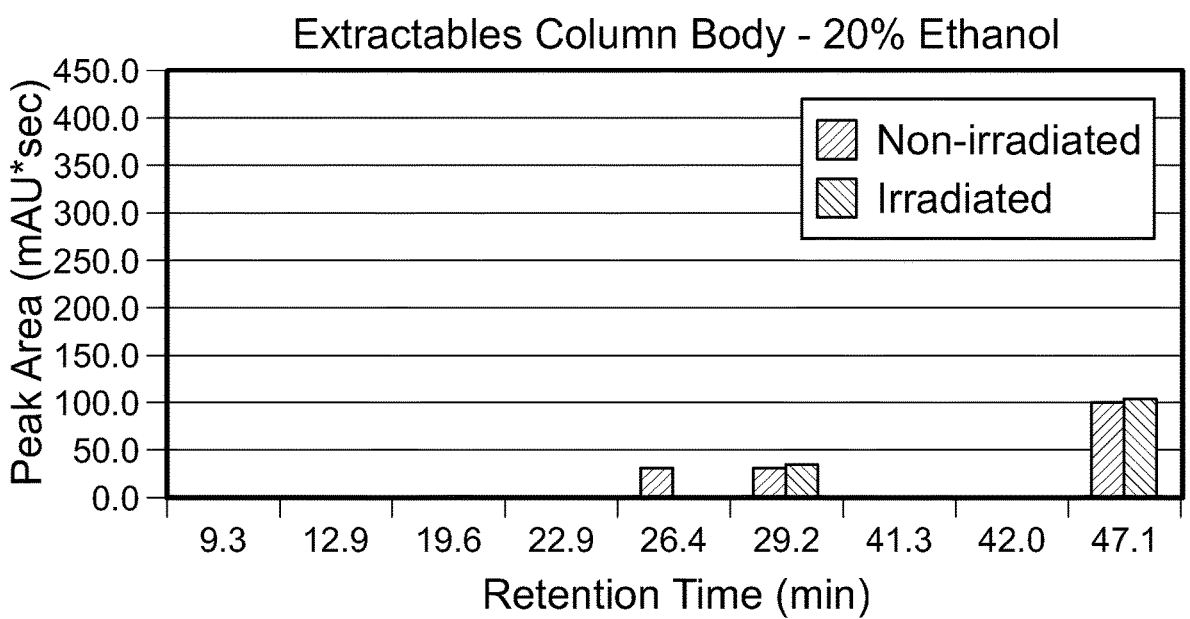
Figure 14D:
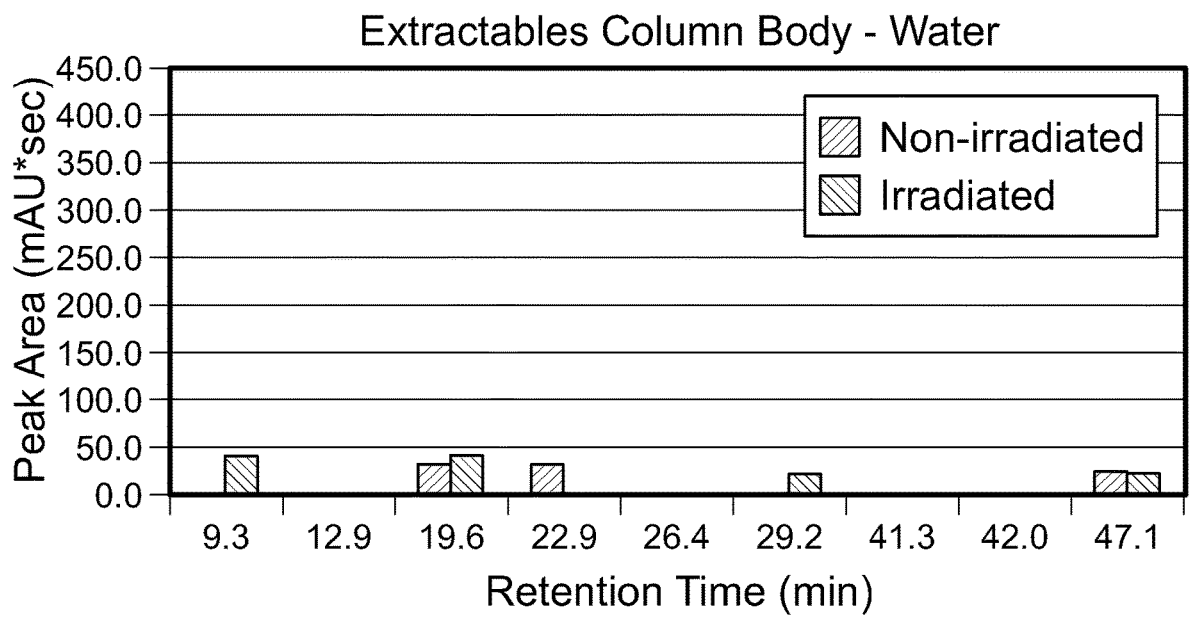
Figure 14E:
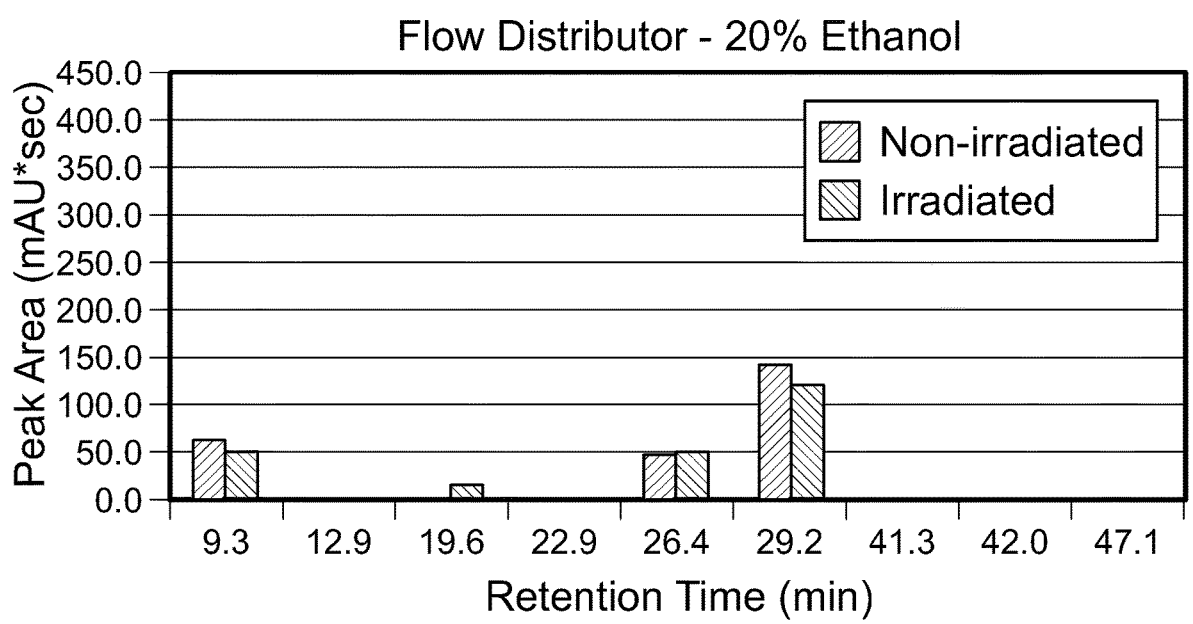
Figure 14F:
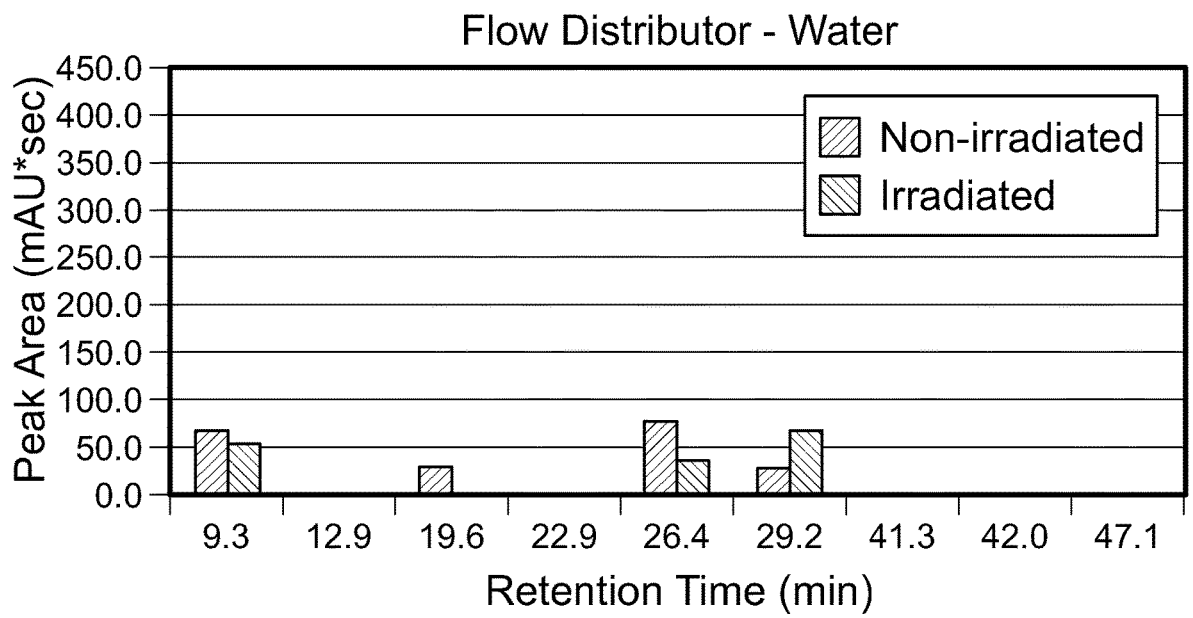
Figure 14G:
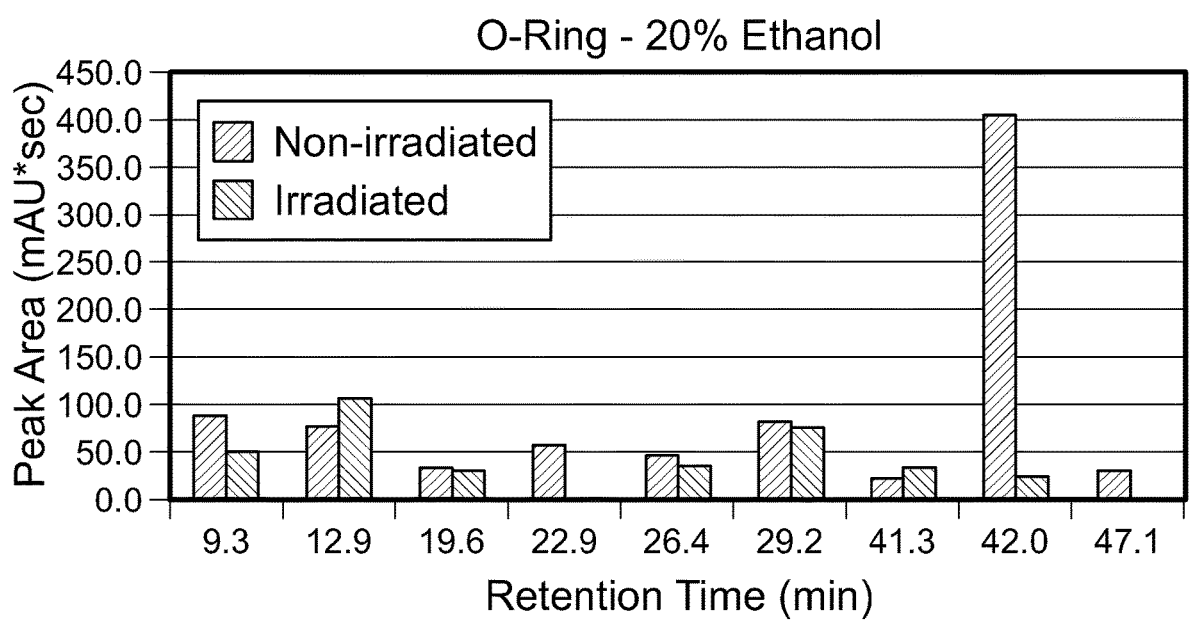
Figure 14H:
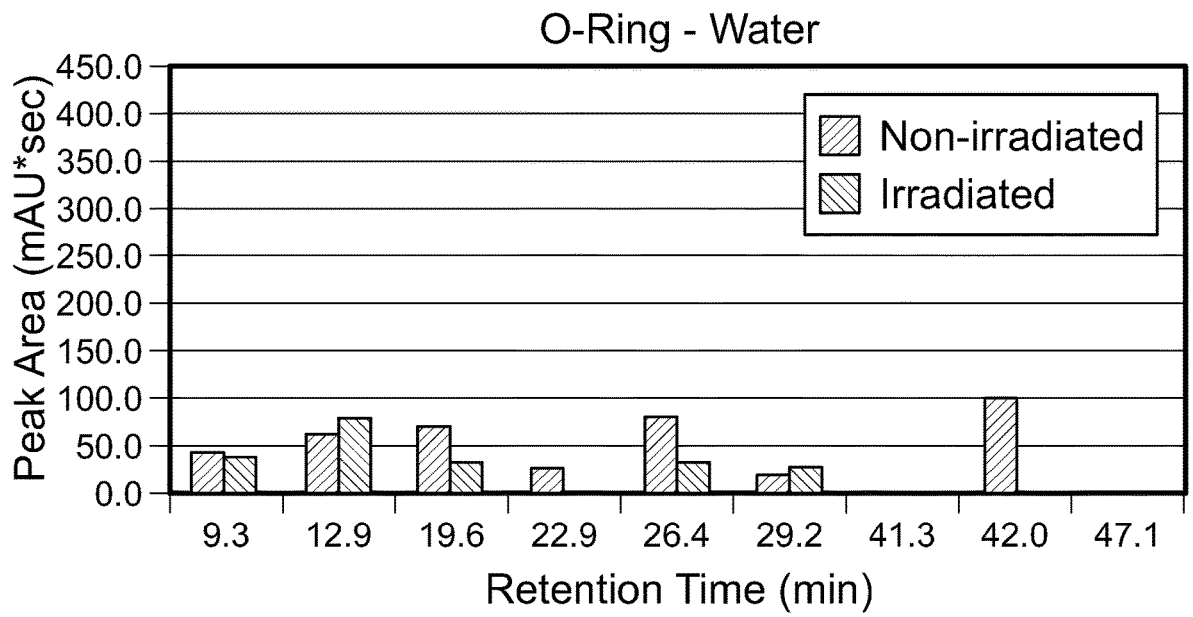
Figure 14I:
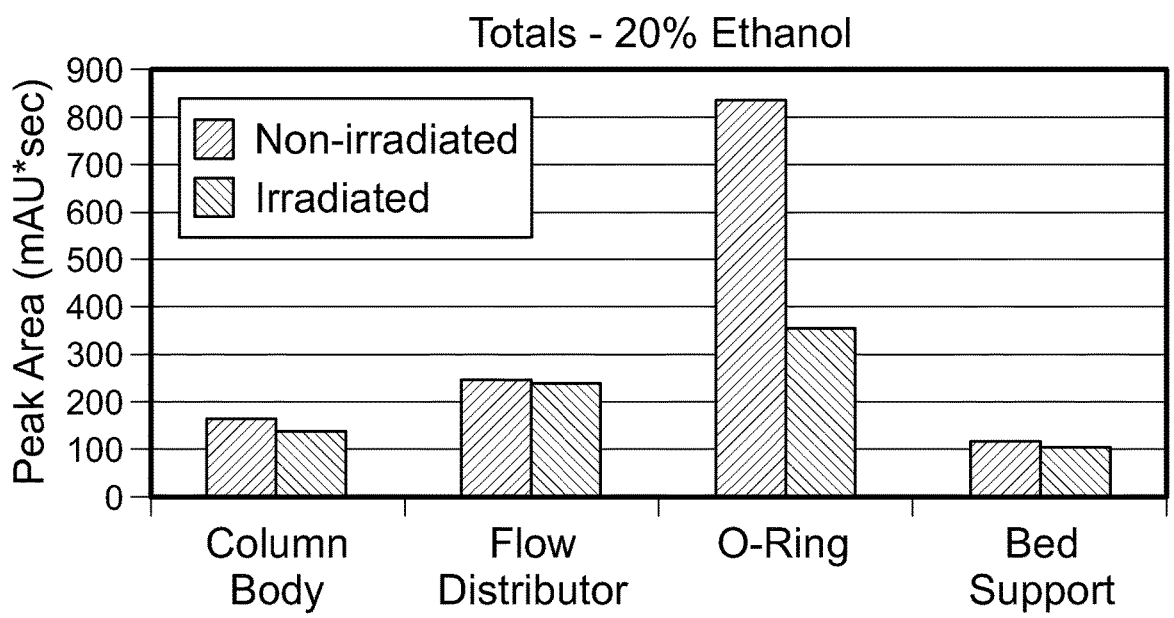
Figure 14J:
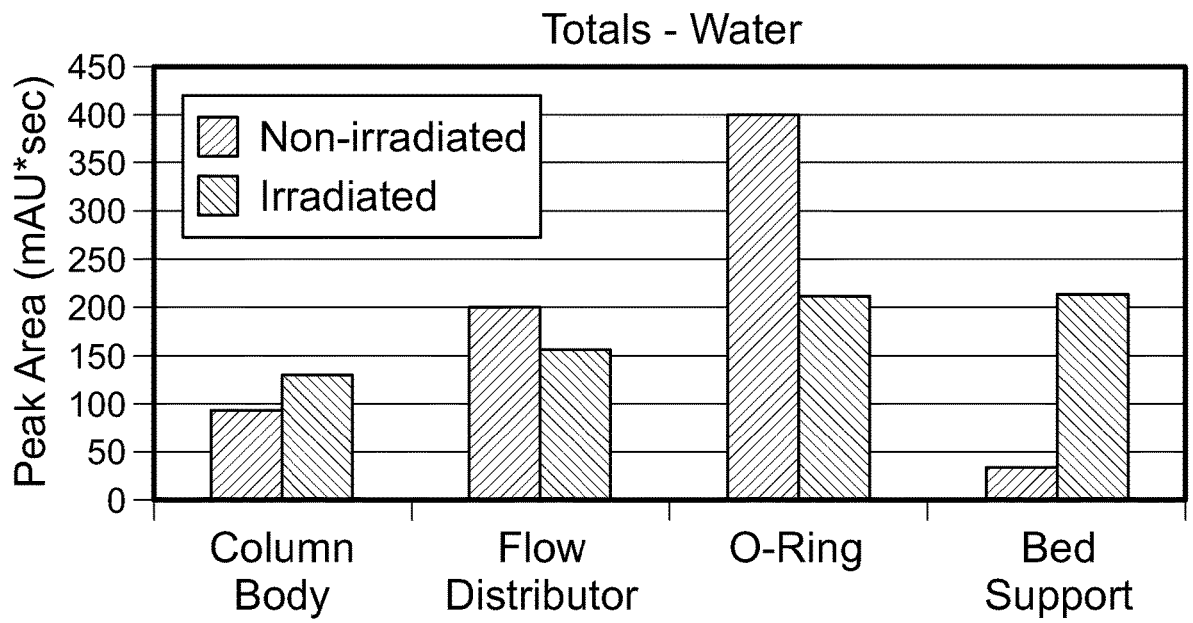

As shown in FIG. 13, the irradiated polypropylene column had an off white/yellow tint as compared to a non-irradiated column, but was otherwise intact.

Example 4—Impact of Gamma Radiation on Mechanical Properties

The purpose of this example was to test the impact of gamma irradiation on the mechanical properties of the chromatography column tube. Specifically, the objective was to derive the stress versus strain curve. The Tensile Strength at Yield, Elongation at Yield, Tensile Stress at Break, Elongation at Break, and Modulus of Elasticity are all found from this curve.

Column Materials
OPUS™ chromatography column (Repligen Corporation)
14 cm extruded polypropylene tube
Methods An OPUS™ chromatography column tube was gamma irradiated between 15-40 kGy with a desired target of 25 kGy of gamma radiation by STERIS Isomedix (Northborough, Mass.). The actual dose delivered was between 21.3-25.3 kGy.

After irradiation, Intertek PTL (Pittsfield, Mass.) performed tensile testing according to ASTM D638-10. Five samples of non-irradiated pure extruded PP tube and five samples of Irradiated, extruded PP tube were prepared (cut from column tube) and tested. The specific parameters are listed below.

Figure 15:
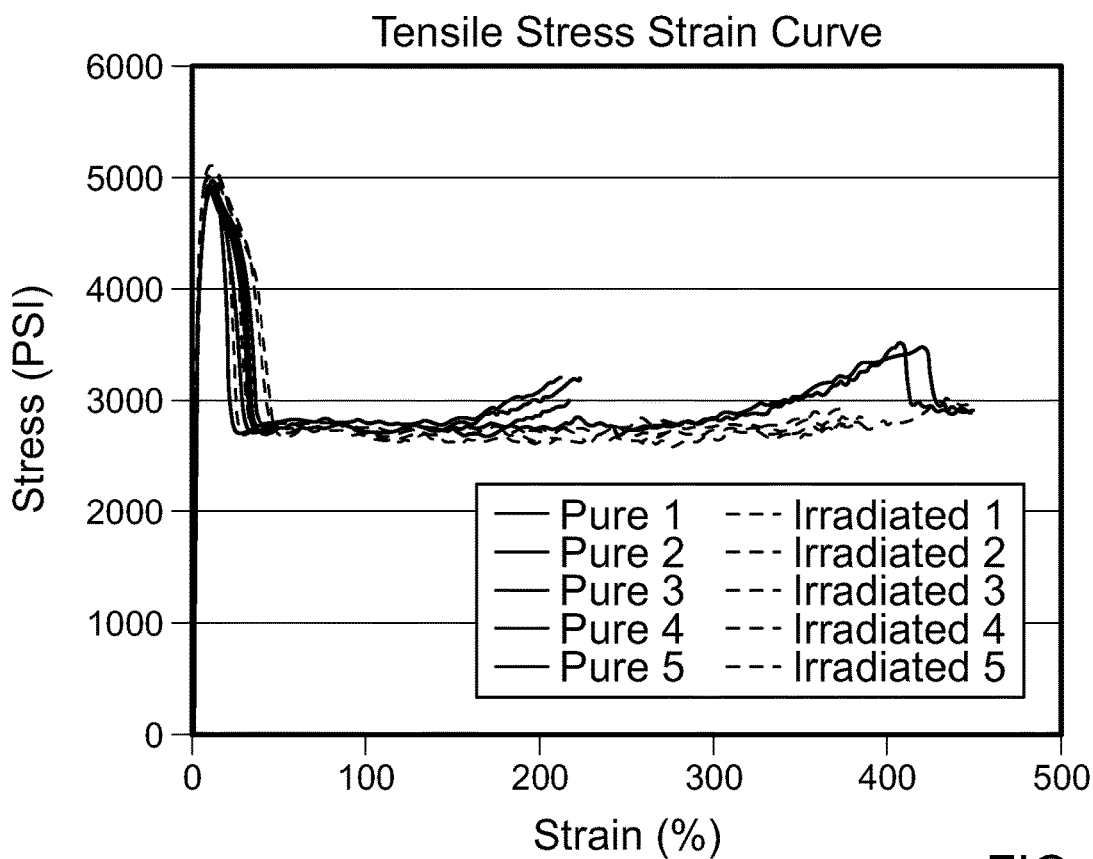
FIG. 15 is a plot illustrating tensile stress strain curves of pure polypropylene and irradiated polypropylene.
Figure 16:
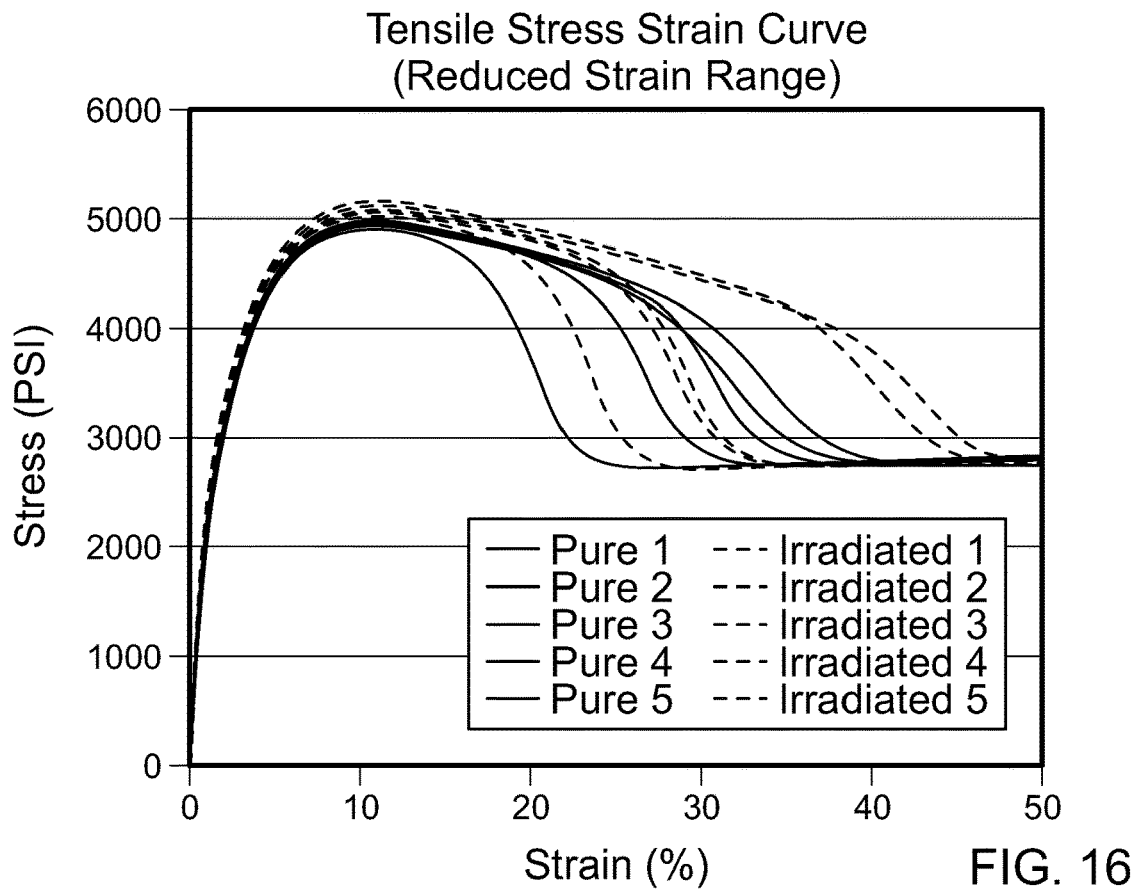
FIG. 16 is a plot illustrating tensile stress strain curves (reduced strain range) of pure polypropylene and irradiated polypropylene.

Sample Preparation
Machined by Intertek PTL
Sample Type
ASTM Type 1 Tensile Bar
Sample Dimensions
0.500"×0.125" (Avg)
Cross-Head Speed
50 mm/min
Extensometer
160% based on 50 mm gage length. Meets minimum requirements for Practice E83: Modulus (Class B-2)/Elongation (Class C)
Conditioning
40+ hours at 23° C.±2° C./50%±10% RH
Test Conditions
23° C.±2° C./50%±10% RH
Results Table 2 summarizes the data obtained from this series of experiments. FIGS. 15 and 16 show negligible differences between the pure and irradiated extruded PP tubes. All samples experienced a very similar looking elastic deformation region represented by the first minimum to maximum shown in FIG. 16. The irradiated samples tend to stretch a little farther for each incremental change in stress after yield which would be characteristic of a tougher material (area under the curve up to break), but the only relevant material is contained in the elastic region of the curve since the plastics will not experience permanent deformation in assembly. All interferences were designed such that the materials will not experience any plastic deformation. It is worthwhile to note that the materials will experience slight creep over time as a result of being in tension or compression, which is a normal physical property of plastics.

Table 2 compares the resulting engineering properties of the pure and irradiated extruded PP tubes as a result of analyzing FIG. 16. Both samples experienced identical elongation at yield, while the irradiated samples achieved a slightly greater, 140 PSI, tensile strength at yield. This is less than 3% of the total tensile strength at yield, so it can be considered a minimal factor, especially considering the standard deviation of the pure and irradiated samples was 35 and 49 PSI, respectively. The modulus of elasticity, which is represented by the slope of the stress versus strain curve in the region of the elastic deformation, is 20,000 PSI higher for the irradiated sample versus the pure sample. A high modulus of elasticity is representative of a more resilient material, thus the material can absorb a higher magnitude of energy and still return to its original shape. The resiliency of a material is represented by the Equation below.

$$U_r = \int_0^{\varepsilon_y} \sigma d\varepsilon$$

where $U_r$ is the Modulus of Resilience, σ is the Stress, ε is the strain, and $\varepsilon_y$ is the value of the strain at yield.

In conclusion, both materials showed very similar elastic deformation, but the irradiated sample would be considered to be more resilient than the non-irradiated pure sample. This means the irradiated sample would require a little more pressure than the non-irradiated pure sample to reach the magnitude of strain to achieve the yield point.

TABLE 2

Analysis of Tensile Properties of Pure and Irradiated extruded PP tube

| Sample Name | Sample Number | Tensile Strength at Yield (PSI) | Elongation at Yield (%) | Tensile Stress at Break (PSI) | Elongation at Break (%) | Modulus of Elasticity (PSI) |
|---|---|---|---|---|---|---|
| Pure PP tube | 1 | 4960 | 11 | 3210 | 220 | 219000 |
| | 2 | 4910 | 11 | 3210 | 210 | 218000 |
| | 3 | 4990 | 11 | 3000 | 220 | 225000 |
| | 4 | 5000 | 11 | 2940 | 450 | 217000 |
| | 5 | 4960 | 11 | 2910 | 450 | 212000 |
| | Avg | 4960 | 11 | 3050 | 310 | 218000 |
| | St Dev | 35 | 0 | 146 | 128 | 4700 |
| Irradiated PP tube | 1 | 5120 | 11 | 2930 | 370 | 239000 |
| | 2 | 5110 | 11 | 2790 | 390 | 232000 |
| | 3 | 5150 | 11 | 2860 | 390 | 242000 |
| | 4 | 5080 | 11 | 2710 | 160 | 240000 |
| | 5 | 5020 | 11 | 2970 | 450 | 235000 |
| | Avg | 5100 | 11 | 2850 | 350 | 238000 |
| | St Dev | 49 | 0 | 100 | 110 | 4000 |

Example 5—Impact of Gamma Radiation on Mechanical Properties

The purpose of this example was to test the impact of gamma radiation on the mechanical properties of the chromatography column tube. Specifically, the objective was to derive the stress versus strain curve. The Flexural Stress and 5% Strain and Flexural Modulus are both found from this curve.

Figure 17:
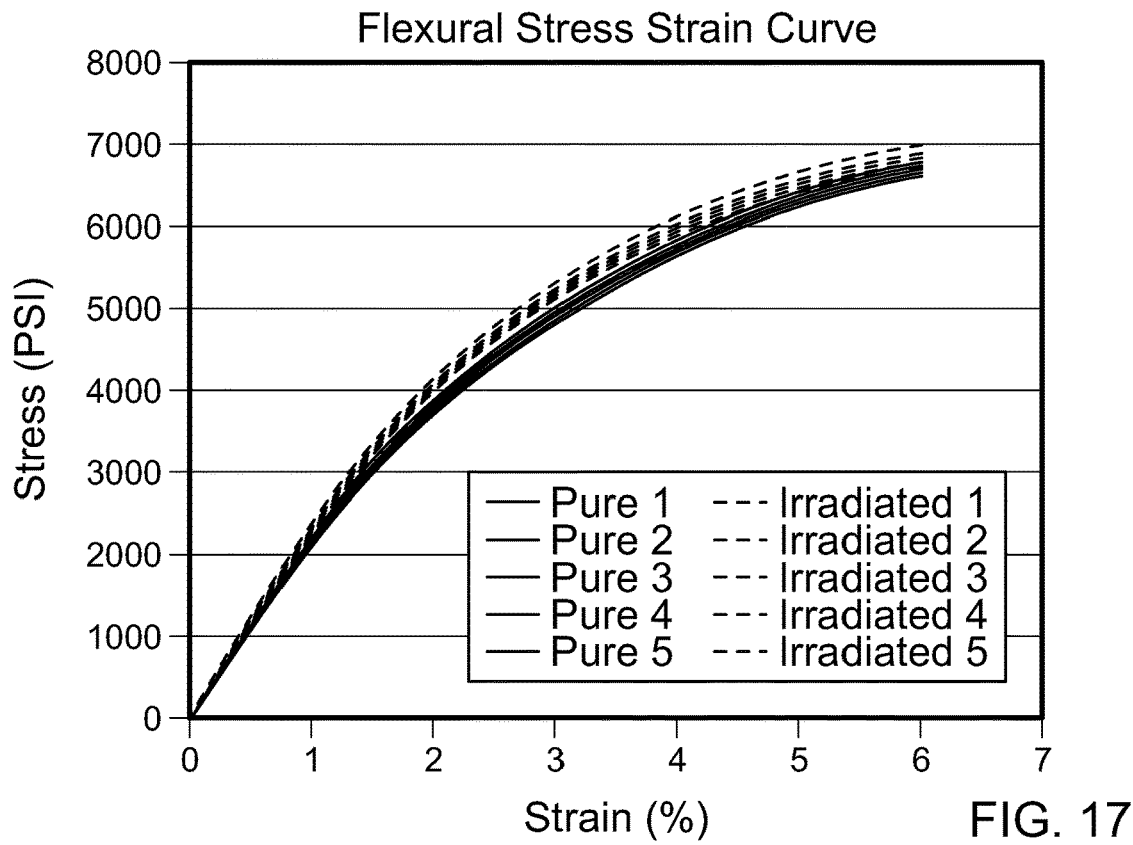
FIG. 17 is a plot illustrating flexural stress strain curves of pure polypropylene and irradiated polypropylene.

Column Materials
OPUS™ chromatography column (Repligen Corporation)
14 cm extruded polypropylene tube.
Methods
An OPUS™ chromatography column tube was gamma irradiated between 15-40 kGy with a desired target of 25 kGy of gamma radiation by STERIS Isomedix (Northborough, Mass.) as described in Example 1. The actual dose delivered was between 21.3-25.3 kGy.
After irradiation, Intertek PTL (Pittsfield, Mass.) performed flexural testing according to ASTM D790-10. Five samples of pure extruded polypropylene tube and five samples of irradiated, extruded polypropylene tube were prepared (cut from column tube) and tested. The specific parameters are listed below.
Sample Preparation
Machined by Intertek PTL
Sample Type
ASTM Flex Bar
Sample Dimensions
0.500"×0.125"×5" (Avg)
Cross-Head Speed
0.054 in/min
Span Length
2.016 in
Extensometer
160% based on 50 mm gage length. Meets minimum requirements for Practice E83: Modulus (Class B-2)/Elongation (Class C)
Span to Depth Ratio
16±1:1
Radius of Supports
0.197 in
Radius of Loading Nose
0.197 in
Conditioning
40+ hours at 23° C.±2° C./50%±10% RH
Test Conditions
23° C.±2° C./50%±10% RH
Results FIG. 17 shows negligible differences between the pure and irradiated extruded PP tubes. A three point bend test was conducted on all samples up to a 6% strain and the irradiated samples required slightly higher pressure to stretch the same distance as pure samples.

Table 3 compares the resulting engineering properties of the pure and irradiated extruded PP tubes as a result of analyzing FIG. 17. Once again as expected, the irradiated samples experienced a slightly higher flexural modulus than the pure samples, which is an indicator that the extruded PP tube became slightly more resilient upon introduction to radiation.

In conclusion, there was a very minimal difference between the pure and irradiated samples as is represented by FIG. 17. The irradiated sample became slightly more resilient after experiencing radiation. Table 3 supports the assumptions previously stated.

TABLE 3

Flexural Stress Properties of Pure and Irradiated Extruded PP Tubes

| Sample Name | Sample Number | Flexural Stress at 5% Strain (PSI) | Flexural Modulus (PSI) |
|---|---|---|---|
| Pure PP tube | 1 | 6390 | 223000 |
| | 2 | 6250 | 215000 |
| | 3 | 6310 | 221000 |
| | 4 | 6410 | 221000 |
| | 5 | 6280 | 220000 |
| | Avg | 6330 | 220000 |
| | St Dev | 69 | 3000 |
| Irradiated PP tube | 1 | 6650 | 235000 |
| | 2 | 6580 | 239000 |
| | 3 | 6510 | 236000 |
| | 4 | 6430 | 233000 |
| | 5 | 6680 | 236000 |
| | Avg | 6570 | 236000 |
| | St Dev | 100 | 2200 |

Example 6—Impact of Gamma Radiation on Mechanical Properties—Flow Distributor O-Rings The purpose of this example was to test gamma radiation impact on the mechanical properties of the chromatography column silicone O-ring. Specifically, the objective was to derive the stress versus strain curve for each material. The Tensile Strength at Break and Elongation at Break are all found from this curve.

Column Materials
14 cm flow distributor O-ring
14 cm extruded polypropylene tube
Methods Assembled OPUS™ chromatography column tubes with flow distributors and O-rings were gamma irradiated between 15-40 kGy with a desired target of 25 kGy of gamma radiation by STERIS Isomedix (Northborough, Mass.). The actual dose delivered was between 21.3-25.3 kGy.

After irradiation, Intertek PTL (Pittsfield, Mass.) performed tension testing according to ASTM D412-06a. Two samples of pure silicone O-ring and two samples of irradiated silicone O-ring were prepared and tested. The tested O-rings were removed from an assembled column that underwent the irradiation process. As such, the O-rings had been in both tension and compression for an extended period of time as well as being under tension and compression during the irradiation process. The pure O-ring was taken from inventory for testing as well. The specific parameters are listed below.

Figure 18:
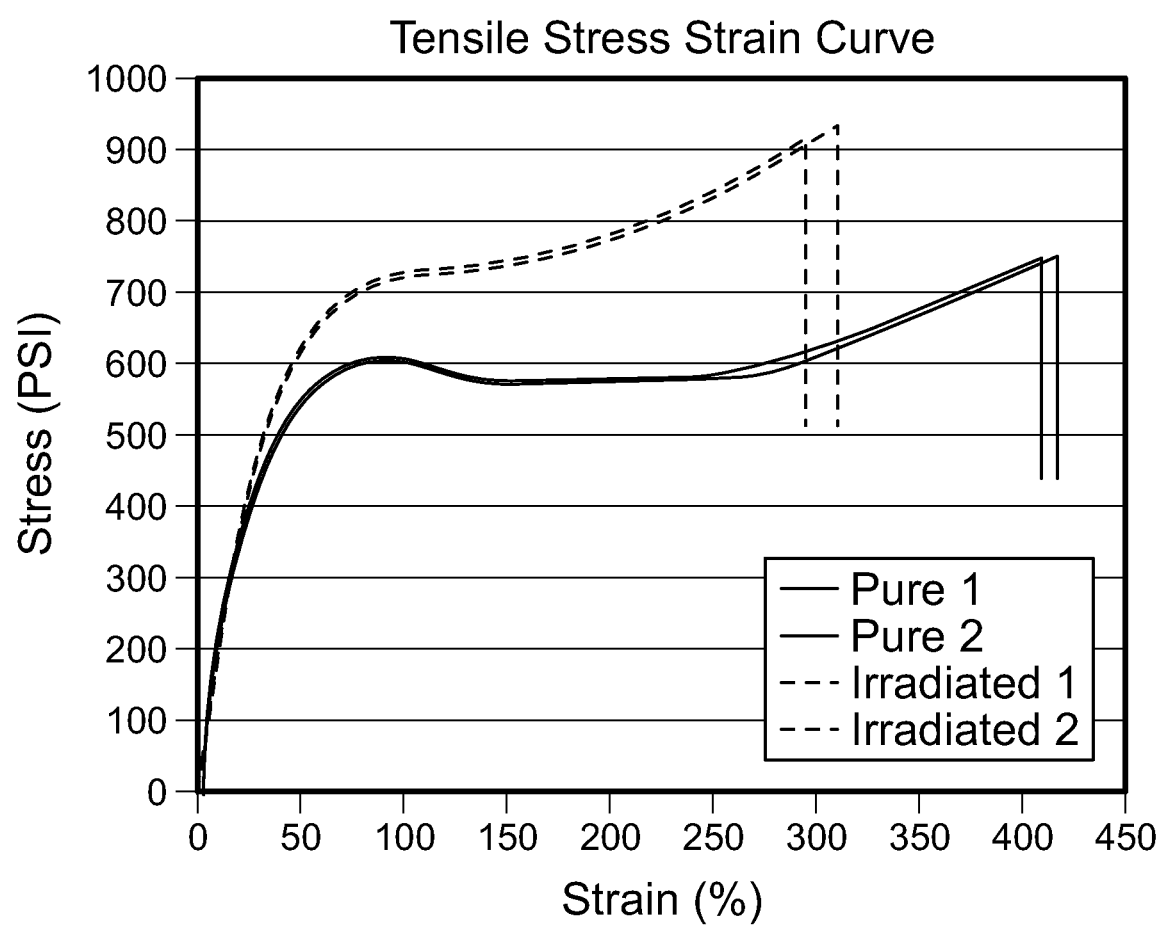
FIG. 18 is a plot illustrating tensile stress strain curves of pure polypropylene and irradiated polypropylene.

Sample Preparation
Cut by Intertek PTL
Sample Type
Pieces of O-ring
Cross-Head Speed
20 in/min
Extensometer
1000% based on 1.0" gage length
Conditioning
40+ hours at 23° C.±2° C./50%±10% RH
Test Conditions
23° C.±2° C./50%±10% RH
Results FIG. 18 represents the stress versus strain curve for the non-irradiated pure and irradiated Silicone O-rings. The non-irradiated pure O-rings were taken from inventory before testing compared to the irradiated sample which had been removed from an assembled column that had been irradiated. In other words, the irradiated sample had experienced compression between the tube walls and the flow distributor (approximately 20% compression) and tension (stretched to fit into the O-ring gland in the flow distributor), which may have contributed to some internal creep in the material. The internal creep would produce a slightly longer sample that would not stretch as far to yield, which is evident in FIG. 17. The irradiated sample also has a steeper elastic region (elastic modulus), higher yield and break stress, and lower strain to break point, which are all evident of a slightly tougher and more resilient material. The combination of radiation and initial compression/tension made the irradiated sample slightly more resilient and tougher than the pure Silicone O-ring. Table 4 supports the assumptions previously stated.

TABLE 4

Analysis of Tensile Strength of Irradiated and Non Irradiated Silicone O-rings

| Sample Name | Sample Number | Diameter (in) | Tensile Strength at Break (PSI) | Elongation at Break (%) |
|---|---|---|---|---|
| Pure Silicone O-ring | 1 | 0.213 | 752 | 420 |
| | 2 | 0.213 | 751 | 410 |
| | Avg | 0.213 | 752 | 415 |
| | St Dev | 0 | .5 | 5 |
| Irradiated Silicone O-ring | 1 | 0.200 | 933 | 310 |
| | 2 | 0.200 | 918 | 300 |
| | Avg | 0.200 | 926 | 305 |
| | St Dev | 0 | 8 | 5 |

Example 7—Impact of Gamma Radiation on Mechanical Properties—Flow Distributor O-Rings The purpose of this example was to test the impact of gamma radiation on the mechanical properties of the chromatography column silicone O-ring. Specifically, the objective was to derive the hardness value for the O-ring samples.

Column Materials
OPUS™ chromatography column (Repligen Corporation)
14 cm flow distributor O-ring
Methods OPUS™ chromatography column flow distributor O-rings were gamma irradiated between 15-40 kGy with a desired target of 25 kGy of gamma radiation by STERIS Isomedix (Northborough, Mass.) as described in Example 1. The actual dose delivered was between 21.3-25.3 kGy.

After irradiation, Intertek PTL (Pittsfield, Mass.) performed hardness testing according to ASTM D2240-05 (2010). Five samples of non-irradiated pure silicone O-ring and five samples of Irradiated Silicone O-ring were prepared and tested. The specific parameters are listed below.

Sample Preparation
Section cut from O-ring by Intertek PTL
Indention Time Interval
1 second
Indenter Used
A
Conditioning
40+ hours at 23° C.±2° C./50%±10% RH
Test Conditions
23° C.±2° C./50%±10% RH
Results Table 5 compares the hardness rating of the pure and irradiated Silicone O-rings. Material hardness is described by the unit Durometer, which represents the distance that a specified instrument presses into a material, provided a constant force. For example, these tests were run per ASTM D2240 type A scale which specifies a hardened steel rod 1.1-1.5 mm in diameter with a truncated 35° cone. The tip of the cone is pressed into the cut sample from the O-ring with an 8.064 N force. The tip of the cone can extend anywhere from 0-2.54 mm depending on the hardness of the material. If the tip travels 2.54 mm, the material would have a 0 Shore A hardness, conversely if the tip travels 0 mm, the material would have a 100 Shore A hardness.

The irradiated sample had a 73 Shore A hardness and the non-irradiated pure Silicone O-ring had a 77 Shore A hardness. The vendor states that the Silicone O-ring has a 75 Shore A hardness, thus the irradiated and non-irradiated pure samples both are 2 standard deviations off the average value, which can be considered negligible since there is a ±5 error associated with this test.

TABLE 5

Hardness Analysis of Irradiated and Non Irradiated Silicone O-rings

| Sample Name | Sample Number | Thickness (in) | Hardness, Shore A |
|---|---|---|---|
| Pure Silicone O-ring | 1 | 0.204 | 77 |
| | 2 | | 77 |
| | 3 | | 77 |
| | 4 | | 79 |
| | 5 | | 76 |
| | Avg | | 77 |
| | St Dev | | 1 |
| Irradiated Silicone O-ring | 1 | 0.207 | 73 |
| | 2 | | 73 |
| | 3 | | 72 |
| | 4 | | 72 |
| | 5 | | 74 |
| | Avg | | 73 |
| | St Dev | | 71 |

Example 8—Impact of Gamma Radiation on an OPUS™ Column Packed with Agarose Media The objective of this example was to determine if the flow properties of the packed bed would be changed following gamma irradiation Materials and Methods An OPUS™ column (Repligen Corporation) was packed with Sepharose 6 Fast Flow media (GE Healthcare) to dimensions of 20 cm internal diameter (id)×20 cm bed height (BH). Initial tests were performed and then the column was gamma irradiated at STERIS (Northborough, Mass.) with a dose between 36.3 kGy and 39.9 kGy and then re-tested.

For the testing, theoretical plates, asymmetry and pressure were determined at 100 cm/hr. The column was equilibrated in 3 column volumes of 100 mM NaCl before a 1% column volume pulse of a 10% acetone solution was injected onto the column.

TABLE 6

Performance Attributes of a Column Packed Bed pre and Post Gamma Irradiation

| Column Performance | Plates/m | Asymmetry | Pressure @ 100 cm/hr |
|---|---|---|---|
| Pre-Gamma | 3295 | 1.2 | 0.36 bar |
| Post-Gamma | 2785 | 1.3 | 0.31 bar |

Results

The change in number of theoretical plates, asymmetry and pressure drop for the packed bed of the gamma irradiated column was less than 20% each. Results indicate the integrity of a 20 cm ID×20 cm BH OPUS column packed with an agarose media such as Sepharose 6FF remains intact following a sterilizing dose of gamma radiation.

Example 9—Impact of Gamma Radiation on Binding Capacity

The purpose of this testing was to determine the level of functionality of various packing media after gamma irradiation. Silica and agarose media functionalized with Protein A were tested. Capacity for human polyclonal IgG (hIgG) in both a static binding capacity (SBC) and dynamic binding capacity (DBC) mode was used to evaluate the functional impact of gamma irradiation on these affinity packing media.

Methods

Silica media, Davisil® (W.R. Grace) and Sepharose™ 4 Fast Flow features were immobilized with recombinant Protein A, rSPA (Repligen Corp) using a reductive amination chemistry. The same media were also immobilized with a different Protein A ligand, MB4 (Repligen). MB4 is a multimeric recombinant Protein A ligand that includes four B domains, each with a G29A mutation. The Sepharose 4FF immobilized with rSPA is sold by Repligen corporation under the trade name CaptivA™ PriMab™. All media samples were stored in a 20% ethanol solution. Half of the immobilized samples were saved as control, and the other half were sent to STERIS (Northborough, Mass.) for gamma irradiation (28.6-33.5 kGy).

A 100 µl volume of each medium was measured into a 1.5 ml centrifuge tube and washed 3 times with 1 ml phosphate buffered saline (PBS) to equilibrate the media. 1.0 ml of 10 g/L IgG (SeraCare) was added to the medium and allowed to mix end over end for 30 minutes. Following incubation the medium was washed 5 times with 1.0 ml PBS. The hIgG was then eluted by addition of 10 ml 100 mM Phosphate, pH 2.8. The amount of hIgG in the eluate was determined by UV measurement at 280 nm. The binding capacity (gram IgG/L media) was calculated by multiplying the UV280 result by 100 and then dividing by an extinction coefficient of 1.3.

IgG Dynamic Binding Capacity

About 3.42 ml amount of each media was packed into the column creating a bed height of 10 cm (Omnifit, 0.66 cm ID). Each column was packed with PBS at a flow of 2.0 ml/min using an AKTA Explorer FPLC (GE Healthcare). IgG (SeraCare) was diluted to 2.2 mg/ml in PBS and then loaded to the column at a flow velocity providing 3.0 minutes of residence time. The binding capacity was determined at 5% hIgG breakthrough.

Results

The results are shown in Table 7.

TABLE 7

Binding Capacity of Protein A chromatography media Pre and Post Gamma Irradiation

| | SBC (mg/mL) | | | DBC-3 min (mg/mL) | | |
|---|---|---|---|---|---|---|
| Sample | Pre-Gamma | Post-Gamma | % Initial Control | Pre-Gamma | Post-Gamma | % Initial Control |
| CaptivA ™ | 45.0 | 35.1 | 78.0% | 28 | 21.4 | 76.4% |
| Sepharose 4FF-MB4 | 42.9 | 36.9 | 86.1% | 27.5 | 19.2 | 69.8% |
| Silica-rSPA | 48.8 | 42.5 | 87.2% | 38.4 | 34.5 | 89.8% |
| Silica-MB4 | 33.0 | 24.5 | 74.2% | 29.5 | 19.5 | 66.1% |

These results show that the percentage of packing media function post gamma irradiation was between 66.0 and 90.0% of the non-irradiated control samples. This result was unexpectedly high given the high level of gamma irradiation applied (28.6-33.5 kGy). These data also demonstrate that in all media tested greater than 65% of initial capacity was maintained and in some cases greater that 80% of capacity was maintained. This performance would purify from 20 g to 42 g of antibody product per liter of irradiated Protein A media and thus support a protein purification process.

Example 10—Impact of the Media Protective Solution Composition During Gamma Irradiation in Relation to Binding Capacity The purpose of this testing was to determine if the composition of the packing media protective solution during gamma irradiation has an impact on the functional capacity post exposure. Agarose media functionalized with Protein A was Gamma irradiated in multiple different solutions. Capacity for human polyclonal IgG (hIgG) in a dynamic (DBC) mode was used to evaluate the impact of gamma radiation on the performance of these affinity packing media in the dynamic binding assay.

Methods

13×20 ml samples of CaptivA™ PriMab™ (Sepharose 4FF immobilized with rSPA, Repligen Corporation) Protein A media were washed into 13 different solutions. Each 20 ml sample was prepared at a 50% slurry concentration. Each of the 13 samples were sent to STERIS (Northborough, Mass.) for targeted gamma radiation dose of 40 kGy. The actual dose delivered was between 36.3 kGy and 39.9 kGy. Following gamma irradiation the DBC was determined for each.

IgG Dynamic Binding Capacity

About 1 ml amount of each media was packed into a column (XK5, 0.5 cm ID). Each column was packed with PBS at a flow of 1 ml/min using an AKTA Explorer FPLC (GE Healthcare). hIgG (SeraCare) was diluted to 2.2 mg/ml in PBS and then loaded to the column at a flow velocity providing 6 minutes of residence time. The binding capacity was determined at 10% hIgG breakthrough.

Results

The results are shown in Table 8.

TABLE 8

Binding Capacity of Protein A chromatography media Gamma Irradiated in different solutions

| Condition | Protective solution | DBC (mg/mL) | % Initial Control |
|---|---|---|---|
| Pre-gamma | 20% ethanol | 38 | — |
| Post-gamma | deionized water | 3 | 7.9% |
| | 20% ethanol, 200 mM ascorbic acid | 26 | 68.4% |
| | 2% benzyl alcohol | 42 | 110.5% |
| | 50 mM acetate, pH 5 | 20 | 52.6% |
| | 50 mM acetate, 2% benzyl alcohol, pH 5 | 21 | 55.3% |
| | 50 mM acetate, 2% benzyl alcohol, 100 mM ascorbic acid, pH 5 | 19 | 50.0% |
| | 50 mM acetate, 2% benzyl alcohol, 200 mM ascorbic acid, pH 5 | 24 | 63.2% |
| | 50 mM acetate, 2% benzyl alcohol, 400 mM ascorbic acid, pH 5 | 24 | 63.2% |
| | 50 mM acetate, pH 6 | 6 | 15.8% |
| | 50 mM acetate, 2% benzyl alcohol, pH 6 | 10 | 26.3% |
| | 50 mM acetate, 2% benzyl alcohol, 100 mM ascorbic acid, pH 6 | 12 | 31.6% |
| | 50 mM acetate, 2% benzyl alcohol, 200 mM ascorbic acid, pH 6 | 13 | 34.2% |
| | Phosphate buffered saline, 2% benzyl alcohol, pH 7 | 42 | 110.5% |

The results indicate the solution in which the Protein A media is gamma irradiated has a major impact on the functional capacity. In deionized water alone the functional capacity is reduced to <10% of original. A prior example showed binding capacity was >65% of control after irradiating in 20% ethanol at a dose between 28.6-33.5 kGy. This indicates that an aliphatic primary alcohol can be beneficial in maintaining performance of affinity media containing Protein A molecules. A similar result was obtained in this experiment with 200 mM ascorbic acid present in a 20% ethanol solution.

Unexpectedly media irradiated in solutions with 2% benzyl alcohol, which did not contain acetate or ethanol, retained all of the functional binding. This provides evidence that the presence of an aromatic alcohol during the gamma radiation exposure may provide a protective advantage. Samples with acetate present were less stable at pH 6 than pH 5 but each retained more capacity compared to water alone. The presence of ascorbic acid in the acetate samples provided a moderate protective effect with increasing concentration.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, embodiments, and modifications are within the scope of the following claims.

What is claimed is:

1. A method of preparing a sterilized packed chromatography column, the method consisting of:
   (a) selecting a tube;
   (b) adding a packing medium into the tube and adding a protective solution to the packing medium, wherein the protective solution comprises 2.0% (v/v) benzyl alcohol in water or phosphate buffered saline and does not comprise acetate or ethanol;
   (c) closing both ends of the tube to create a packed column; and
   (d) irradiating the column with a dose of gamma radiation of from at least 8 kGy to about 40 kGy to create a sterilized packed chromatography column, wherein (a) the packing medium is functionalized with *Staphylococcus* Protein A (SpA) polypeptides capable of binding to immunoglobulin IgG, and (b) following gamma irradiation in the protective solution, the packed column has a Sterility Assurance Level (SAL) of $10^{-3}$ organisms/column and the packing medium retains all of its functional binding for IgG at 10% breakthrough.

* * * * *